United States Patent [19]
Baucke et al.

[11] Patent Number: 6,114,358
[45] Date of Patent: Sep. 5, 2000

[54] THROMBIN INHIBITORS

[75] Inventors: Dorit Baucke, Mannheim; Udo Lange; Helmut Mack, both of Ludwigshafen; Werner Seitz, Plankstadt; Thomas Zierke, Böhl-Iggelheim; Hans Wolfgang Höffken, Ludwigshafen; Wilfried Hornberger, Neustadt, all of Germany

[73] Assignee: BASF Aktiengesellschaft, Ludwigshafen, Germany

[21] Appl. No.: 09/242,289

[22] PCT Filed: Jul. 29, 1997

[86] PCT No.: PCT/EP97/04104

§ 371 Date: Feb. 10, 1999

§ 102(e) Date: Feb. 10, 1999

[87] PCT Pub. No.: WO98/06741

PCT Pub. Date: Feb. 19, 1998

[30] Foreign Application Priority Data

Aug. 14, 1996 [DE] Germany ............... 196 32 773

[51] Int. Cl.$^7$ ............... A61K 31/44; A61K 31/40; A61K 31/42; A61K 31/41; A61K 31/415
[52] U.S. Cl. ............... 514/336; 514/422; 514/374; 514/364; 514/365; 514/378; 514/406; 548/527; 548/517; 548/131; 548/236; 548/375.1; 548/524; 548/518; 548/204; 548/247; 546/280.4
[58] Field of Search ............... 548/517, 236, 548/527, 375.1, 131, 247, 204; 546/280.4; 514/422, 374, 364, 336, 406, 365, 378

[56] References Cited

FOREIGN PATENT DOCUMENTS

| | | |
|---|---|---|
| 601459 | 6/1994 | European Pat. Off. |
| 94/29336 | 12/1994 | WIPO |
| 95/23609 | 9/1995 | WIPO |
| 95/35309 | 12/1995 | WIPO |
| 96/25426 | 8/1996 | WIPO |
| 98/06740 | 2/1998 | WIPO |

*Primary Examiner*—Zinna Northington Davis
*Assistant Examiner*—Binta Robinson
*Attorney, Agent, or Firm*—Keil & Weinkauf

[57] ABSTRACT

Compounds of the formula $$A-B-E-D-C(=NH)(NH_2)$$

where A, B, E and D have the meanings indicated in the description, and their preparation are described. The substances are suitable for controlling diseases.

16 Claims, No Drawings

THROMBIN INHIBITORS

This is a 371 of PCT/EP97/04104, filed Jul. 29, 1997.

The present invention relates to novel five-membered heterocyclic amidines, to their preparation and to their use as competitive inhibitors of trypsin-like serine proteases, especially thrombin and kininogenases such as kallikrein. The invention also relates to pharmaceutical compositions which contain the compounds as active ingredients, and to the use of the compounds as thrombin inhibitors, anticoagulants and antiinflammatory agents.

Thrombin belongs to the group of serine proteases and plays a central part in the blood coagulation cascade as terminal enzyme. Both the intrinsic and the extrinsic coagulation cascade lead via a plurality of amplifying stages to the production of thrombin from prothrombin. Thrombin-catalyzed cleavage of fibrinogen to fibrin then initiates blood coagulation and aggregation of platelets which, in turn, due to the binding of platelet factor 3 and coagulation factor XIII, and a large number of highly active mediators, enhance thrombin formation.

The formation and action of thrombin are central events in the development both of white, arterial and of red, venous thrombi and are therefore potentially effective points of attack for drugs. Thrombin inhibitors are, by contrast with heparin, able independently of cofactors completely to inhibit simultaneously the effects of free thrombin and of that bound to platelets. They are able to prevent in the acute phase thromboembolic events after percutaneous transluminal coronary angioplasty (PTCA) and lysis, and to act as anticoagulants in extracorporeal circulation (heart-lung machine, hemodialysis). They can also be used generally for the prophylaxis of thrombosis, for example after surgical operations.

It is known that synthetic arginine derivatives influence the enzymatic activity of thrombin by interacting with the active serine residue of the protease thrombin. Peptides based on Phe-Pro-Arg in which the N-terminal amino acid is in the D form have proven particularly beneficial. D-Phe-Pro-Arg isopropyl ester is described as a competitive thrombin inhibitor (C. Mattson et al., Folia Haematol, 109 (1983) 43–51).

Derivatization of the arginine at the C terminus to the aldehyde leads to an enhancement of the inhibitory effect. Thus, a large number of arginals able to bind the hydroxyl group of the "active" serine in a hemiacetal have been described (EP 185390, 479489, 526877, 542525; WO 93/15756, 93/18060.

The thrombin-inhibitory activity of peptide ketones, fluorinated alkyl ketones and of keto esters, boric acid derivatives, phosphoric esters and α-keto carboxamides can likewise be explained by this serine interaction (EP 118280, 195212, 362002, 364344, 410411, 471651, 589741, 293881, 503203, 504064, 530167; WO 92/07869, 94/08941).

The peptide 4-amidinophenylglycinephosphonate diphenyl esters described by J. Oleksyszyn et al. in J. Med. Chem. 37 (1994) 226–231 are irreversible thrombin inhibitors with inadequate selectivity in respect of other serine proteases.

DE 3 108 810, WO 93/11152 and EP 601 459 describe agmatine and hence arginine derivatives which are unable to interact with the active serine in serine proteases.

WO 94/29336, EP 0 601 459 and WO 95/23609 represent a further development in which the agmatine is replaced by an arylamidine residue.

Kininogenases are serine proteases which liberate vasoactive peptides, called kinins (bradykinin, kallidin and Met-Lys-bradykinin), from kininogens. Kininogens are multifunctional proteins which occur in coagulation and inflammation cascade reactions. As inhibitors, they protect cells from damage by cysteine proteases (Müller Esterl, FEBS Lett. 182 (1985) 310–314). Important kininogenases are plasma kallikrein, tissue kallikrein and mast cell tryptase.

Kinins like bradykinin and kallidin are vasoactive peptides which influence a large number of biological processes. They play an essential part in inflammatory processes. By increasing vascular permeability, they lead to hypotension and edema. Furthermore, they are very potent pain-producing antacoids [sic] and have great importance as cellular mediators in the pathophysiology of asthma, of allergic rhinitis and of arthritis (K. D. Bhoola, C. D. Figueroa, K. Worthy, Pharmacological Revies [sic] 44 (1) (1992)1–80).

Irrespective of the mechanisms underlying inflammatory processes, fluid containing all the protein systems in the circulating blood escapes from blood vessels. This means that escape of plasma fluid from vessels is involved in diseases such as asthma, rhinitis and inflammatory internal diseases. Moreover, mast cell tryptase is released particularly in allergic processes (Salomonson et al., Am. Rev. Respir. Dis. 146 (1992) 1535–1542).

The arginine chloromethyl ketones H-(D)-Pro-Phe-Arg-$CH_2Cl$ and H-(D)-Phe-Phe-Arg-$CH_2$—Cl have been described by Kettner and Shaw as plasma kallikrein inhibitors (Biochem. 17 (1978) 4778–4784 and Meth. Enzym. 80 (1981) 826–842).

Various synthetic derivatives of benzamidines and benzylamines have proven to be inhibitors of plasma kallikrein, with the benzamidines having a considerably stronger inhibitory effect (F. Markward, S. Drawert, P. Walsmann, Biochemical Pharmacology 23 (1974) 2247–2256).

PKSI-527, the hydrochloride of N-(trans-4-aminomethylcyclohexylcarbonyl)-L-phenylalanine 4-carboxymethylanilide, is also an effective inhibitor of this kininogenase (Wanaka, Ohamoto et al., Thromb. Res., 57 (6) (1990) 889–895).

The invention relates to compounds of the formula I

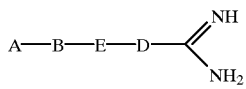

where

A is

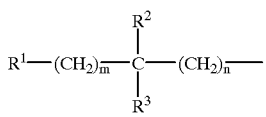

where m is 0, 1 or 2, n is 0, 1 or 2, $R^1$ is HOOC—, $C_{1-6}$-alkyl-OOC—, aryl-OOC— or —OH, $R^2$ is H, $C_{1-4}$-alkyl or $R^1$-$(CH_2)_m$-, $R^3$ is H or $C_{1-4}$-alkyl, B is

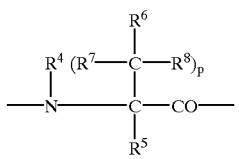

where
R⁴ is H, $C_{1-6}$-alkyl or $R^1$-$(CH_2)_m$- (where $R^1$ and m have the abovementioned meanings),
p is 0 or 1,
R⁵ is H or $C_{1-4}$-alkyl,
R⁶ is H, $C_{1-8}$-alkyl, phenyl which may carry up to three identical or different radicals from the group of $C_{1-4}$-alkyl, $CF_3$, $C_{1-4}$-alkoxy, F or Cl, or $C_{3-8}$-cycloalkyl which may carry up to four identical or different $C_{1-4}$-alkyl radicals, or where one or two C—C single bonds in the ring can be replaced by a C=C double bond, or a phenyl ring can be fused on, $C_7$-$C_{12}$-bicyclo-alkyl or $C_{10}$-tricycloalkyl or
R⁴ and R⁶ together are an ethylene or propylene group,
R⁷ is H, $C_{1-8}$-alkyl, phenyl which may carry up to three identical or different radicals from the group of $C_{1-4}$-alkyl, $CF_3$, $C_{1-4}$-alkoxy, F or Cl, or $C_{3-8}$-cycloalkyl which may carry up to four identical or different $C_{1-4}$-alkyl radicals,
R⁸ is H or $C_{1-4}$-alkyl,
E is

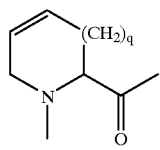

q is 0 or 1
D is

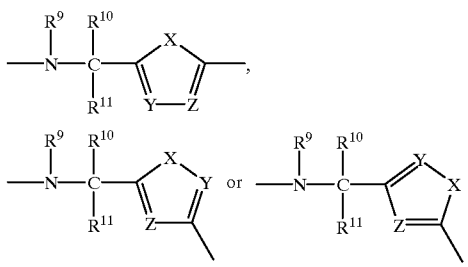

where
R⁹ is H or $C_{1-3}$-alkyl,
R¹⁰ is H or $C_{1-4}$-alkyl,
R¹¹ is H or $C_{1-4}$-alkyl,
X is O, S, —NR¹² (R¹²=H, $C_{1-6}$-alkyl),
Y is —N= or —CR¹³= (R¹³=H, $C_{1-4}$-alkyl, Cl, $CF_3$),
Z is —N= or —CR¹³=,
and the salts thereof with physiologically tolerated acids.

The amino acid derivatives represented by B preferably have the (D) configuration; 3,4-dehydroproline and 4,5-dehydropipecolic acid have the (L) configuration.

Preferred compounds of the formula I are those where A to E have the following meanings:
A is HOOC—$(CH_2)_t$- (t=1, 2 or 3), (HOOC—$CH_2$)$_2$—CH—, (HO—$CH_2$)$_2$CH—, HOOC—$CH_2$—CH(COOH)—, HOOC—CH($CH_2$—$CH_2$—OH)—, HOOC—CH($C_{1-4}$-Alkyl)-, HOOC—C($C_{1-4}$-Alkyl)$_2$-, $C_{1-4}$-Alkyl—OOC—$(CH_2)_t$-,
B is

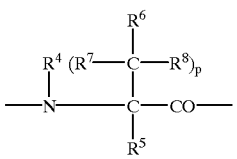

p is 0, 1,
R⁴ is H, $C_{1-4}$-alkyl or HOOC—$(CH_2)_m$- (m=1, 2 or 3),
R⁵ is H, methyl
R⁶ is H, $C_{1-8}$-alkyl, phenyl which may carry up to three identical or different radicals from the group of $CH_3$, $CF_3$, $CH_3$—O, F or Cl, or $C_{3-8}$-cycloalkyl, which may carry up to four methyl radicals, 1,4-cyclohexadienyl, bicyclo[2.2.2]octyl, bicyclo[2.2.1]heptyl, norbornyl, adamantyl, indanyl, decalinyl,
R⁷ is H, $C_{1-8}$-alkyl, phenyl, which may carry up to three identical or different radicals from the group of $CH_3$, $CF_3$, $CH_3O$, F or Cl, or $C_{3-8}$-cycloalkyl which may carry up to four methyl radicals,
R⁸ is H, $C_{1-4}$-alkyl,
(B preferably has the D configuration),
E is

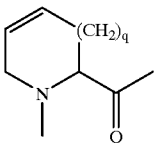

q is 0, 1
(E preferably has the L configuration),
D is

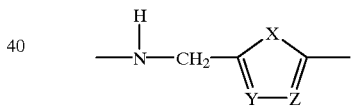

with
X=S, O, NH, $NCH_3$, $NC_2H_5$,
Y=CH, C—$CH_3$, C—Cl, C—$CF_3$ and
Z=CH, C—$CH_3$, C—Cl, C—$CF_3$
or
X=S, O, NH, N—$CH_3$ Y=N
Z=CH, C—$CH_3$, C—$CF_3$
or
X=S, O, NH, N—$CH_3$ Y=CH, C—$CH_3$, C—$CF_3$
Z=N
or
X=S, O, NH, N—$CH_3$ Y=N
Z=N

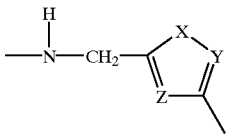

with
X=S, O, NH, $NCH_3$, $NC_2H_5$,

Y=CH, C—CH₃, C—CF₃ and
Z=CH, C—CH₃, C—CF₃, C—Cl
or
X=O, NH, NCH₃
Y=N
Z=CH, C—CH₃, C—CF₃
or
X=O, S, NH, NCH₃
Y=CH, C—CH₃, C—CF₃
Z=N
or
X=O, S, NH, NCH₃
Y=Z=N

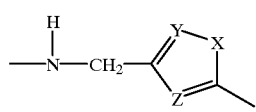

with
X=S, O, NH, NCH₃, NC₂H₅,
Y=CH, C—CH₃, C—CF₃ and
Z=CH, C—CH₃, C—CF₃, C—Cl
or
X=O, NH, NCH₃
Y=N
Z=CH, C—CH₃, C—CF₃, C—Cl
or
X=O, S, NH, NCH₃
Y=CH, C—CH₃, C—CF₃
Z=N
C—CF₃
or
X=O, NH, NCH₃
Y=Z=N.

Particularly preferred compounds of the formula I are those where A, B, D and E have the following meanings A is HOOC—CH₂, HOOC—CH₂—CH₂, HOOC—CH(CH₃), HOOC—CH(C₂H₅)

B is

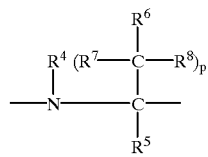

p is 0, 1,
R⁴ is H, CH₃
R⁵ is H, CH₃,
R⁶ is C₁₋₈-alkyl, C₅₋₈-cycloalkyl which may carry up to four methyl radicals, bicyclo[2.2.2]octyl, bicylo[2.2.1]heptyl [sic], norbornyl, adamantyl, indanyl, decalinyl with cyclopentyl, cyclohexyl and cycloheptyl being particularly preferred,
R⁷ is H, CH₃,
R⁸ is H, CH₃, E is

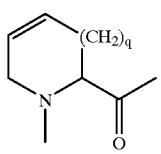

q is 0, 1
D is

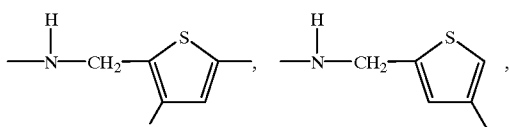
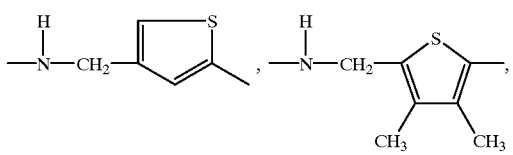
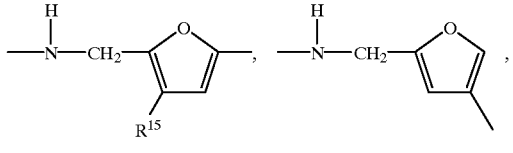
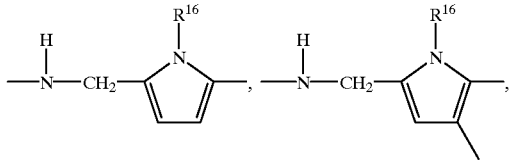
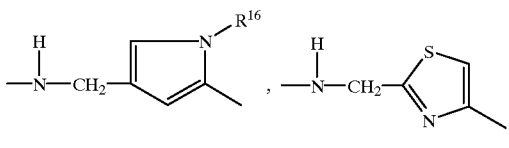
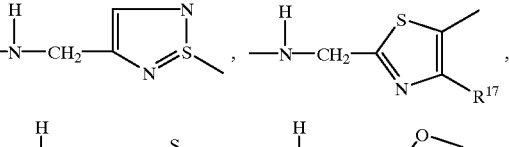
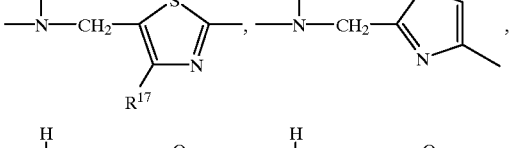
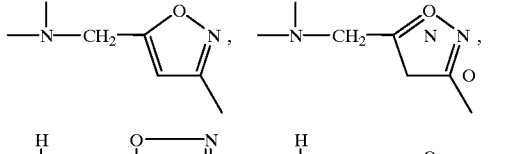
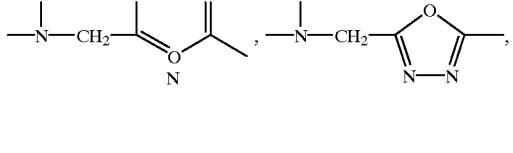

-continued

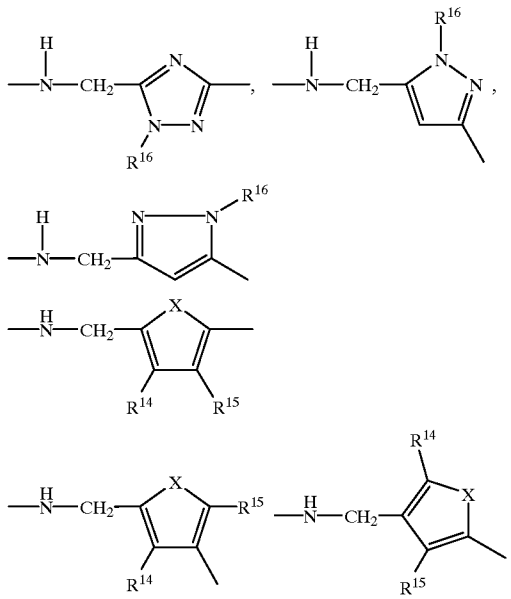

with
R[14]: H, CH₃, Cl, CF₃, preferably H
R[15]: H, Cl, CF₃, preferably H
R[16]: H, CH₃, C₂H₅, preferably CH₃
R[17]: H, CH₃, CF₃, preferably H, CH₃

The following substances are particularly preferred:
tBuOOC—CH₂-(D) Chg-Pyr-NH—CH₂-5-(2-am)-thioph
HOOC—CH₂-(D)Chg-Pyr-NH—CH₂-5-(2-am)-thioph
tBuOOC—CH₂-(D)Chg-Dep-NH—CH₂-5-(2-am)-thioph
HOOC—CH₂-(D)Chg-Dep-NH—CH₂-5-(2-am)-thioph
HOOC—CH₂-(D,L)Cpg-Pyr-NH—CH₂-5-(2-am)-thioph
HOOC—CH₂-(D,L)Cheg-Pyr-NH—CH₂-5-(2-am)-thioph
HOOC—CH₂-(D,L)Cog-Pyr-NH—CH₂₋₅-(2-am)-thioph
HOOC—CH₂-(D,L)Nog-Pyr-NH—CH₂-5-(2-am)-thioph
HOOC—CH₂-(D,L)Adaala-Pyr-NH—CH₂-5-(2-am)-thioph
HOOC—CH₂-(D,L) 4-MeCha-Pyr-NH—CH₂-5-(2-am)-thioph
HOOC—CH₂-(D,L)γ-MeCha-Pyr-NH—CH₂-5-(2-am)-thioph
HOOC—CH₂-(D,L)4-MeChg-Pyr-NH—CH₂₋₅-(2-am)-thioph
HOOC—CH₂-(D,L)3,3-Me₂Chg-Pyr-NH—CH₂-5-(2-am)-thioph
HOOC—CH₂-(D,L)3,3-Me₂Cha-Pyr-NH—CH₂-5-(2-am)-thioph
HOOC—CH₂-(D,L)4-iPrChg-Pyr-NH—CH₂-5-(2-am)-thioph
HOOC—CH₂-(D,L)3,4,5(MeO)₃Phe-Pyr-NH—CH₂₋₅-(2-am)-thioph
HOOC—CH₂-(D,L)Chea-Pyr-NH—CH₂-5-(2-am)-thioph
HOOC—CH₂-(D )Diphe-Pyr-NH—CH₂-5-(2-am)-thioph
HOOC—CH₂-(D,L )ββ-Me₂Cha-Pyr-NH—CH₂-5-(2-am)-thioph
HOOC—CH₂-(D,L)Adagly-Pyr-NH—CH₂₋₅-(2-am)-thioph
HOOC—CH₂-(D,L)-1-Tic-Pyr-NH—CH₂-5-(2-am)-thioph
HOOC—CH₂-(D,L)Dch-Pyr-NH—CH₂₋₅-(2-am)-thioph
HOOC—CH₂-(D,L)4-iPrCha-Pyr-NH—CH₂-5-(2-am)-thioph
HOOC—CH₂-(D)α-MeCha-Pyr-NH—CH₂-5-(2-am)-thioph
HOOC—CH₂-(D)α-MeCha-Dep-NH—CH₂-5-(2-am)-thioph
HOOC—CH₂-(N—Me)(D)Cha-Pyr-NH—CH₂₋₅-(2-am)-thioph
HOOC—CH₂-(D)Cha-Pyr-NH—CH₂-5-(2-am)-thioph
HOOC—CH₂-(D)Cha-Dep-NH—CH₂-5-(2-am)-thioph
HOOC—CH₂-(D)Cha-Pyr-NH—CH₂₋₄-(2-am)-thioph
HOOC—CH₂-(D)Cha-Dep-NH—CH₂₋₄-(2-am)-thioph
HOOC—CH₂-(D)Cha-Pyr-NH—CH₂-5-(3-am)-thioph
HOOC—CH₂-(D)Cha-Dep-NH—CH₂-5-(3-am)-thioph
HOOC—CH₂-(D)Chg-Pyr-NH—CH₂-5-(3-am)-thioph
HOOC—CH₂-(D)Chg-Pyr-NH—CH₂₋₄-(2-am)-thioph
HOOC—CH₂-(D)Cha-Pyr-NH—CH₂₋₅-(2-am)-fur
HOOC—CH₂-(D)Cha-Dep-NH—CH₂₋₅-(2-am)-fur
HOOC—CH₂-(D)Cha-Pyr-NH—CH₂₋₄-(2-am)-fur
HOOC—CH₂-(D)Cha-Dep-NH—CH₂₋₄-(2-am)-fur
HOOC—CH₂-(D)Cha-Pyr-NH—CH₂-5-(3-am)-fur
HOOC—CH₂-(D)Cha-Dep-NH—CH₂-5-(3-am)-fur
HOOC—CH₂-(D)Chg-Pyr-NH—CH₂-5-(2-am)-fur
HOOC—CH₂-(D)Chg-Pyr-NH—CH₂-5-(3-am)-fur
HOOC—CH₂-(D)Cha-Pyr-NH—CH₂-5-(1-Me-2-am)-pyrr
HOOC—CH₂-(D)Chg-Pyr-NH—CH₂-5-(1-Me-2-am)-pyrr
HOOC—CH₂-(D)Cha-Dep-NH—CH₂-5-(1-Me-2-am)-pyrr
HOOC—CH₂-(D)Cha-Pyr-NH—CH₂-4-(1-Me-2-am)-pyrr
HOOC—CH₂-(D)Cha-Dep-NH—CH₂-4-(1-Me-2-am)-pyrr
HOOC—CH₂-(D)Cha-Pyr-NH—CH₂-5-(1-Me-3-am)-pyrr
HOOC—CH₂-(D)Cha-Dep-NH—CH₂-5-(1-Me-3-am)-pyrr
HOOC—CH₂-(D)Cha-Pyr-NH—CH₂-5-(2-am-3,4-Me₂)-thioph
HOOC—CH₂-(D)Cha-Pyr-NH—CH₂-5-(2-am-3-Me)-thioph
HOOC—CH₂-(D)Cha-Pyr-NH—CH₂-5-(2-am-4-Me)-thioph
HOOC—CH₂-(D)Cha-Pyr-NH—CH₂-5-(2-am-3-Me)-fur
HOOC—CH₂-(D)Cha-Pyr-NH—CH₂-5-(2-am-4-Me)-fur
HOOC—CH₂-(D)Cha-Pyr-NH—CH₂-5-(3-am-2-Me)-fur
HOOC—CH₂-(D)Cha-Pyr-NH—CH₂-2-(5-am)-thiaz
HOOC—CH₂-(D)Cha-Pyr-NH—CH₂-2-(4-am)-thiaz
HOOC—CH₂-(D)Cha-Pyr-NH—CH₂-4-(2-am)-thiaz
HOOC—CH₂-(D)Cha-Pyr-NH—CH₂-5-(2-am)-thiaz
HOOC—CH₂-(D)Chg-Pyr-NH—CH₂-2-(5-am)-thiaz
HOOC—CH₂-(D)Chg-Pyr-NH—CH₂-2-(4-am)-thiaz
HOOC—CH₂-(D)Chg-Pyr-NH—CH₂-4-(2-am)-thiaz
HOOC—CH₂-(D)Chg-Pyr-NH—CH₂-5-(2-am)-thiaz
HOOC—CH₂-(D)Cha-Dep-NH—CH₂-2-(5-am)-thiaz
HOOC—CH₂-(D)Cha-Pyr-NH—CH₂-2-(4-am)-oxaz
HOOC—CH₂-(D)Chg-Pyr-NH-CH₂-2-(4-am-)-oxaz
HOOC—CH₂-(D)Chg-Pyr-NH-CH₂-2-(4-am-)-oxaz
HOOC—CH₂-(D)Cha-Pyr-NH—CH₂-5-(3-am-1-Me)-pyraz
HOOC—CH₂-(D)Cha-Pyr-NH—CH₂-3-(5-am)-1,2,4-oxadiaz
HOOC—CH₂-(D)Cha-Pyr-NH—CH₂-5-(3-am)-1,2,4-oxadiaz
HOOC—CH₂-(D)Chg-Pyr-NH—CH₂-5-(3-am)-1,2,4-oxadiaz
HOOC—CH₂-(D)Cha-Pyr-NH—CH₂-5-(3-am-1-Me)-1,2,4-triaz
HOOC—CH₂-CH₂-(D)Cha-Pyr-NH—CH₂-5-(2-am)-thioph
HOOC—CH₂-CH₂-(D)Cha-Pyr-NH—CH₂-5-(2-am)-fur
HOOC—CH₂-CH₂-(D)Cha-Pyr-NH—CH₂-5-(1-Me-2-am)-pyrr
(HOOC—CH₂)₂-(D)Cha-Pyr-NH—CH₂-5-(2-am)-thioph
(HOOC—CH₂)₂CH-(D)Cha-Pyr-NH—CH₂-5-(2-am)-thioph
HOOC—CH₂-(D)Chg-Pyr-NH—CH₂-5-(2-am)-1,3,4-thiadaz HOOC—CH$_2$-(D)Cha-Pyr-NH—CH$_2$-5-(2-am)-1,3,4-thiadaz
HOOC—CH$_2$-(D)Chg-Pyr-NH—CH$_2$-5-(2-am)-1,3,4-oxadiaz
HOOC—CH$_2$-(D)Cha-Pyr-NH—CH$_2$-5-(2-am)-1,3,4-oxadiaz List of Abbreviations
Adaala: Adamantylalanine
Adagly: Adamantylglycine
AIBN: Azobisisobutyronitrile
Ac: Acetyl
Ala: Alanine
am: Amidino
Asp: Aspartic acid
Aze: Azetidinecarboxylic acid
Bn: Benzyl
Boc: tert-Butyloxycarbonyl
Bu: Butyl
Cbz: Benzyloxycarbonyl
Cha: Cyclohexylalanine
Chea: Cycloheptylalanine
Cheg: Cycloheptylglycine
Chg: Cyclohexylglycine
Cog: Cyclooctylglycine
Cpa: Cyclopentylalanine
Cpg: Cyclopentylglycine
DCC: Dicyclohexylcarbodiimide
Dch: Dicyclohexylalanine
Dcha: Dicyclohexylamine
DCM: Dichlormethane
Dep: 4,5-Dehydropipecolic acid
DMF: Dimethylformamide
DIPEA: Diisopropylethylamine
Dpa: Diphenylalanine
Diphe: 2,5-Dihydrophenylalanine
Et: Ethyl
Eq: Equivalents
fur: Furan
Gly: Glycine
ham: Hydroxyamidino
HOSucc: Hydroxysuccinimide
HPLC: High performance liquid chromatography
Hyp: Hydroxyproline
imi: Imidazole
2-Ind: 2-Dihydroindolecarboxylic acid
iPr: iso-Propyl
Leu: Leucine
Me: Methyl
α-MeCha: α-Methylcyclohexylalanine
ββ-Me$_2$Cha: 2-Amino-3-cyclohexyl-3-methylbutyric acid or ββ-Dimethylcyclohexylalanine
4-MeCha: (4-Methyl-1-cyclohexyl)alanine
γ-MeCha: (1-Methyl-1-cyclohexyl)alanine
3,3-Me$_2$Cha: (3,3-Dimethyl-1-cyclohexyl)alanine
4-MeChg: (4-Methyl-1-cyhexyl)glycine [sic]
3,3-Me$_2$Chg: (3,3-Dimethyl-1-cyclohexyl)glycine
MPLC: Medium pressure liquid chromatography
MTBE: Methyl tert-butyl ether
NBS: N-Bromosuccinimide
Nog: Norbornylglycine
Oxadiaz: 1,2,4-Oxadiazole
Oxaz: Oxazole
Ph: Phenyl
Phe: Phenylalanine
2Phi: 2-Perhydroindolecarboxylic acid
Pic: Pipecolic acid
pico: Picolyl
pim: Piperidinylmethyl
PPA: Propylphosphonic anhydride
Pro: Proline
Py: Pyridine
Pyr: 3,4-Dehydroproline
pyraz: Pyrazole
pyrr: Pyrrole
RT: Room temperature
RP-18: Reversed Phase C-18
t: Tertiary
tBu: Tertiary butyl
tert: Tertiary
TBAB: Tetrabutylammonium bromide
TEA: Trietylamine [sic]
TFA: Trifluoroacetic acid
TFFA: Trifluoroacetic anhydride
TLC: Thin layer chromatography
thiaz: Thiazole
thioph: Thiophene
1Tic: 1-Tetrahydroisoquinolinecarboxylic acid
3Tic: 3-Tetrahydroisoquinolinecarboxylic acid
TOTU: O-(Cyanoethoxycarbonylmethylene)amino]-N,N,N',N'-tetramethyluronium [sic] tetrafluoroborate
triaz: 1,3,4-Triazole
Z: Benzyloxycarbonyl The invention furthermore relates to compounds which comprise the structural element

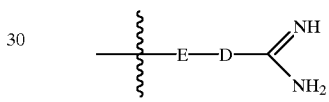

where E and D have the abovementioned meanings, and there is on the nitrogen atom of E a hydrogen atom, a protective group, an unsubstituted or substituted natural or unnatural amino acid, an unsubstituted or substituted carboxylic acid or sulfonic acid or an unsubstituted or substituted alkyl radical. The structural fragment is valuable as constituent of serine protease inhibitors and especially of thrombin and kallikrein inhibitors.

The invention furthermore relates to the intermediates of the formula IIa and IIb

where A, B, E and D have the meanings indicated in claim 1.

The novel intermediates are used to prepare the compounds I and are valuable building blocks for synthesizing serine protease inhibitors.

The compounds of the formula I can exist as such or in the form of their salts with physiologically tolerated acids. Examples of such acids are: hydrochloric acid, citric acid, tartaric acid, lactic acid, phosphoric acid, methanesulfonic acid, acetic acid, formic acid, maleic acid, fumaric acid, succinic acid, hydroxy-succinic acid, sulfuric acid, glutaric acid, aspartic acid, pyruvic acid, benzoic acid, glucuronic acid, oxalic acid, ascorbic acid and acetylgylcine.

The novel compounds of the formula I can be employed for the following indications:
  diseases whose pathogenetic mechanism derives directly or indirectly from the proteolytic effect of thrombin,
  diseases whose pathogenetic mechanism derives from thrombin-dependent activation of receptors and signal transductions, diseases associated with stimulation [eg. by PAI-1, PDGF (platelet derived growth factor), P-selectin, ICAM-1, tissue factor] or inhibition (eg. NO synthesis in smooth muscle cells) of the expression of genes in body cells, diseases deriving from the mitogenic effect of thrombin, diseases deriving from a thrombin-dependent change in the contractility and permeability of epithelial cells (eg. vascular endothelial cells), thrombin-dependent thromboembolic events such as deep vein thrombosis, pulmonary embolism, myocardial or cerebral infarct, atrial fibrillation, bypass occlusion, disseminated intravascular coagulation (DIC), reocclusion and for reducing the reperfusion time on comedication with thrombolytics such as streptokinase, urokinase, prourokinase, t-PA, APSAC, plasminogen activators from the salivary glands of animals, and the recombinant and mutated forms of all these substances, the occurrence of early reocclusion and late restenosis after PTCA, the thrombin-dependent proliferation of smooth muscle cells, the accumulation of active thrombin in the CNS (eg. in Alzheimer's disease), tumor growth and to prevent adhesion and metastasis of tumor cells.

The novel compounds can be used in particular for the therapy and prophylaxis of thrombin-dependent thromboembolic events such as deep vein thromboses, pulmonary embolisms, myocardial or cerebral infarcts and unstable angina, also for the therapy of disseminated intravascular coagulation (DIC). They are furthermore suitable for combination therapy with thrombolytics such as streptokinase, urokinase, prourokinase, t-PA, APSAC and other plasminogen activators to shorten the reperfusion time and extend the reocclusion time.

Further preferred areas of use are to prevent thrombin-dependent early reocclusion and late restenosis after percutaneous transluminal coronary angioplasty, to prevent thrombin-induced proliferation of smooth muscle cells, to prevent accumulation of active thrombin in the CNS (eg. in Alzheimer's disease), to control tumors and to prevent mechanisms which lead to adhesion and metastasis of tumor cells.

The novel compounds can also be used for coating artificial surfaces such as hemodialysis membranes and the tubing systems and lines necessary therefor, and of oxygenators in extravascular circulation, stents and heart valves.

The novel compounds can furthermore be employed for diseases whose pathogenetic mechanism derives directly or indirectly from the proteolytic effect of kininogenases, especially kallikrein, eg. in inflammatory diseases such as asthma, pancreatitis, rhinitis, arthritis, urticaria and other internal inflammatory diseases.

The compounds according to the invention can be administered in a conventional way orally or parenterally (subcutaneously, intravenously, intramuscularly, interperitoneally, rectally). Administration can also take place with vapors or sprays through the nasopharyngeal space.

The dosage depends on the age, condition and weight of the patient and on the mode of administration. As a rule, the daily dose of active substance per person is about 10–2000 mg on oral administration and about 1–200 mg on parenteral administration. This dose can be given in 2 to 4 single doses or once a day as depot form.

The novel compounds can be used in conventional solid or liquid pharmaceutical forms, eg. as uncoated or (film-) coated tablets, capsules, powders, granules, suppositories, solutions, ointments, creams or sprays. These are produced in a conventional manner. The active substances can for this purpose be mixed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain from 0.1 to 99% by weight of active substance.

Experimental Part

The compounds of the formula I can be prepared as shown in Schemes I–III.

Building blocks A, B, E and D are preferably assembled separately beforehand and employed in suitably protected form (see Scheme I–III).

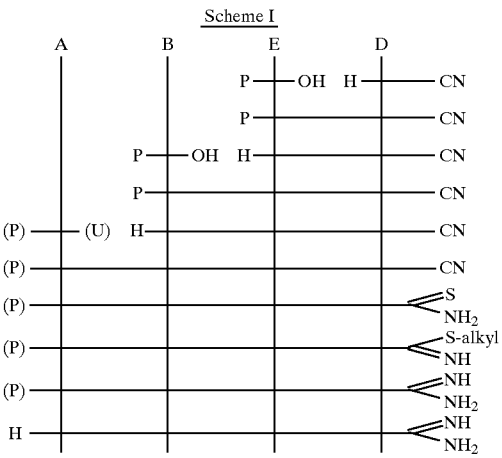

(P=protective group, (P)=protective group or H)

Scheme I describes linear assemblage of the molecule I by coupling the amine H-D-CN to the N-protected amino acid P-E-OH to give P-E-D-CN, eliminating the N-terminal protective group to give H-E-D-CN, coupling to the N-protected amino acid P-B-OH to give P-B-E-D-CN, eliminating the protective group P to give H-B-E-D-CN, subsequently alkylating with the unprotected or protected (P)-A-U building block (U=leaving group) or reductively alkylating with (P)-A'-U (U=aldehyde, ketone) or Michael addition with a suitable (P)-A"-C=C— derivative to give (P)-A-B-E-D-CN. Conversion of the nitrile functionality into the amidine group takes place either by the classical Pinner synthesis (R. Boder, D. G. Neilson, Chem. Rev. 61 (1962) 179) or by a modified Pinner synthesis which proceeds via imino thioester salts as intermediate (H. Vieweg et al., Pharmazie 39 (1984) 226) or directly by the method of A. Eschenmoser Helv. Chimica Acta 69 (1986) 1224. Subsequently the protective groups still present in the molecule are eliminated, preferably by acid hydrolysis.

If building block D is incorporated as H-D-CONH$_2$ into the synthesis, dehydration of the amide to the nitrile functionality, or the conversion into the thioamide functionalities takes place on one of the protected intermediates. As an alternative, the building block D may be employed as H-D-CSNH$_2$ in the synthesis.

Scheme II

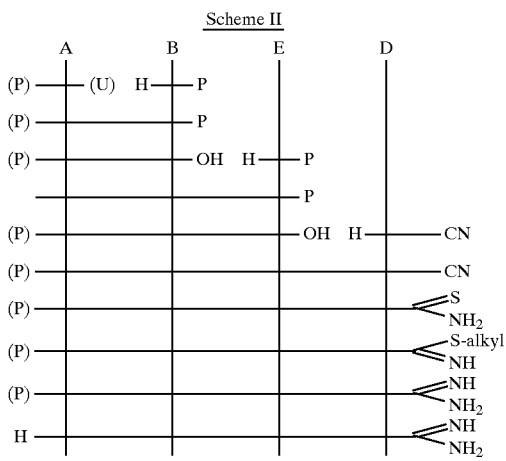

Scheme II describes linear assemblage of the molecule I by alkylation, reductive animation [sic] or Michael addition of H-B-P onto appropriately suitable unprotected or protected A building blocks to give (P)-A-B-P, elimination of the C-terminal protective group to give (P)-A-B-OH, coupling is [sic] H-E-P to give (P)-A-B-E-P, elimination of the C-terminal protective group to give (P)-A-B-E-OH, coupling to H-D-CN to give (P)-A-B-E-D-CN and reaction of this intermediate to give the final product as in Scheme I.

Where compounds (P)-A-B-P still have a free NH functionality on B, this must be provided with a suitable protective group before elimination of the C-terminal protective group. The protective groups used in each case must be orthogonal to one another.

As an alternative to the H-D-CN building block, it is also possible to employ H-D-CONH$_2$, H-D-CSNH$_2$, H-D-C(NH) NH$_2$, H-D-C(NP)NH$_2$, H-D-C (NP)NHP, with the coupled intermediate (P)-A-B-E-D-CONH$_2$ in the first case being dehydrated to (P)-A-B-E-D-CN or being directly converted into (P)-A-B-E-D-CSNH$_2$.

Scheme III

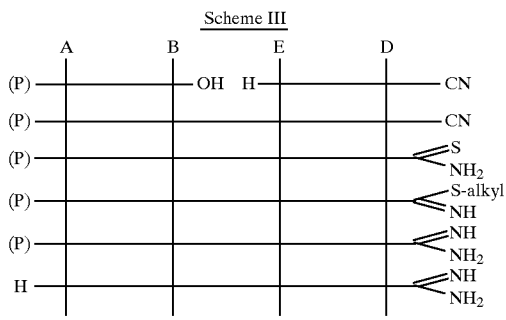

Scheme III describes a very efficient way for preparing compounds I by a convergent synthesis. The appropriately protected building blocks (P)-A-B-OH and H-E-D-CN are coupled together and the resulting intermediate (P)-A-B-E-D-CN is reacted to give the final product as in Scheme I.

As an alternative to H-E-D-CN, it is also possible to employ H-E-D-CONH$_2$ or H-E-D-CSNH$_2$, and in the first case the coupled intermediate (P)-A-B-E-D-CONH$_2$ is dehydrated to (P)-A-B-E-D-CN or converted into (P)-A-B-E-D-CSNH$_2$.

The N-terminal protective groups employed are Boc, Cbz or Fmoc, preferably Boc, and the C-terminal protective groups are methyl, tert-butyl and benzyl. If a plurality of protective groups is present in the molecule, they must be orthogonal to one another if they are not to be eliminated simultaneously. If the intermediates contain building block E, the Cbz and benzyl protective groups are unsuitable.

The required coupling reactions and the other reactions for introducing and eliminating protective groups are carried out under standard conditions of peptide chemistry (see M. Bodanszky, A. Bodanszky "The Practice of Peptide Synthesis", 2nd edition, Springer Verlag Heidelberg, 1994).

Boc protective groups are eliminated using dioxane/HCl or TPA/DCM, and Cbz protective groups are eliminated by hydrogenolysis or with HF. Hydrolysis of ester functionalities takes place with LiOH in an alcoholic solvent or in dioxane/water. TFA or dioxane/HU [sic] is used to cleave t-butyl esters.

The reactions were checked by TLC, normally using the following mobile phases:

| A. DCM/MeOH | 95:5 |
| B. DCM/MeOH | 9:1 |
| C. DCM/MeOH | 8:2 |
| D. DCM/MeOH/50% HOAc | 40:10:5 |
| E. DCM/MeOH/50% HOAc | 35:15:5 |

Where separations by column chromatography are mentioned, these were separations on silica gel using the abovementioned mobile phases.

Reversed phase HPLC separations were carried out with acetonitrile/water and HOAc buffer.

The starting compounds can be prepared by the following methods:

Examples of building blocks A employed for the alkylation are tert-butyl α-bromoacetate, tert-butyl β-bromopropionate, tert-butyl α-bromopropionate, tert-butyl γ-bromobutyrate, tert-butyl α-bromobutyrate, THP-protected bromoethanol, THP-protected γ-bromopropanol, α-bromo-γ-butyrolactone, for the reductive amination are dihydroxyacetone, di-tert-butyl acetonedicarboxylate, and for the Michael addition are tert-butyl acrylate, tert-butyl methacrylate, di-tert-butyl fumarate. Those of said tert-butyl esters which cannot be purchased are prepared by methods similar to G. Uray, W. Lindner, Tetrahedron, 44 1988 4357–4362.

B Building Blocks

A wide variety of possibilities is available in the literature for the general and specific synthesis of amino acids. A review thereof is provided by, inter alia, Houben-Weyl, Volume E16d/Part 1, pages 406 et seq.

Precursors which were frequently employed were benzophenone imine acetic acid ethyl ester [sic], diethyl acetamidomalonate and ethyl isonitrileacetate [sic].

Various glycine and alanine derivatives were prepared, for example, starting from ethyl isonitrileacetate [sic] and an appropriate ketone or aldehyde (see H.-J. Prätorius, J. Flossdorf, M.-R. Kula Chem. Ber. 108 (1975) 3079).

The syntheses of cyclooctylglycine, 2-norbornylglycine, adamantylalanine, γ-methylcyclohexylalanine, 4-isopropyl-1-cyclohexylalanine, 4-methyl-1-cyclohexylalanine and 4-methyl-1-cyclohexylglycine were carried out via the corresponding ethyl 2-formylaminoacrylates (U. Schöllkopf and R. Meyer, Liebigs Ann. Chem. 1977, 1174) starting from ethyl isocyanoacetate with the relevant carbonyl compounds cyclooctanone, 2-norbornanone, 1-formyladamantane, 1-formyl-1-methylcyclohexane, 1-formyl-4-iso-propylcyclohexane, 1-formyl-4-methylcyclohexane and 4-methylcyclohexanone by the following general methods:

General Method for Synthesizing Ethyl 2-Formylaminoacrylates

A solution of 100 mmol of ethyl isocyanoacetate in 50 ml of THF was added dropwise to 100 mmol of potassium tert-butoxide in 150 ml of THF at 0 to −10C. After 15 min at the same temperature 100 mmol of the appropriate carbonyl compound in 50 ml of THF were added, the reaction mixture was allowed slowly to rise to RT, and the solvent was stripped off in a rotary evaporator. The residue was mixed with 50 ml of water, 100 ml of acetic acid and 100 ml of DCM, and the product was extracted with DCM. The DCM phase was dried over $Na_2SO_4$, and the solvent was stripped off in a rotary evaporator. The products resulted almost pure but could, if necessary, be purified further by column chromatography on silica gel (mobile phases: ether/petroleum ether mixtures).

General Method for Amino Acid Hydrochlorides Starting from the Ethyl 2-Formylaminoacrylates 100 mmol of the ethyl 2-formylaminoacrylates were hydrogenated with Pd/C (10%) and hydrogen in 200 ml of glacial acetic acid until the reaction was complete. The catalyst was then filtered off, the acetic acid was stripped off as far as possible in a rotary evaporator, and the residue was refluxed in 200 ml of 50% concentrated hydrochloric acid for 5 h. The hydrochloric acid was stripped off in a rotary evaporator, and the product was dried at 50° C. under reduced pressure and then washed several times with ether. The hydrochlorides resulted as pale colored crystals.

25.0 g of cyclooctylglycine hydrochloride were obtained starting from 18.9 g (150 mmol) of cyclooctanone. 26.6 g of 2-norbornylglycine hydrochloride were obtained starting from 16.5 g (150 mmol) of 2-norbornanone. 26.0 g of adamantylalanine hydrochloride were obtained starting from 19.7 g (120 mmol) of 1-formyladamantane. 16.6 g of γ-methylcyclohexylalanine hydrochloride were obtained starting from 12.6 g (100 mmol) of 1-formyl-1-methylcyclohexane. 25.9 g of 4-methylcyclohexylglycine hydrochloride were obtained starting from 16.8 g (150 mmol) of 4-methylcyclohexanone. 18 g of trans-4-methyl-1-cyclohexylalanine hydrochloride were obtained starting from 15 g of trans-1-formyl-4-methylcyclohexane. 10 g of 3,3-dimethyl-1-cyclohexylalanine hydrochloride were obtained starting from 9 g of 3,3-dimethyl-1-formylcyclohexane.

The aldehyde 1-formyl-3,3-dimethylcyclohexane required for the synthesis is prepared by a method based on those of Moskal and Lensen (Rec. Trav. Chim. Pays-Bas 106 (1987) 137–141).

A solution of n-butyllithium in n-hexane (72 ml, 115 mmol) was added dropwise over the course of 10 min to a stirred solution of diethyl isocyanomethylphosphonate (17 ml, 105 mmol) in 280 ml of anhydrous diethyl ether at −60° C. The resulting suspension was then stirred at −60° C. for 15 min and, over the course of 10 min, a solution of 3,3-dimethylcyclohexanone (13 g, 105 mmol) in 100 ml of anhydrous diethyl ether was added, keeping the temperature below −45° C. The reaction mixture was allowed to reach 0° C. and, after stirring at this temperature for 90 min, 150–200 ml of 38% strength aqueous hydrochloric acid were cautiously added. The mixture was vigorously stirred at room temperature for 15 h to complete the hydrolysis. The organic phase was separated off and washed with 200 ml each of water, saturated sodium bicarbonate solution and saturated sodium chloride solution. It was dried over magnesium sulfate, filtered and concentrated in a rotary evaporator in order to remove the solvent. The resulting residue was employed without further purification as starting material for synthesizing the amino acid.

Boc-(D)-α-methylcyclohexylalanine 3.4 g (12.2 mmol) of Boc-(D)-α-methyl-Phe-OH were hydrogenated in 100 ml of MeOH in the presence of 250 mg of 5% Rh on $Al_2O_3$ under 10 bar of hydrogen at 50° C. for 24 h. Filtration and stripping off the solvent resulted in 2.8 g of Boc-(D)-α-methyl-Cha-OH. $^1$H-NMR (DMSO-d$^6$, δ in ppm): 12 (very broad signal, COOH); 1.7–0.8 (25 H; 1.35 (s, Boc), 1.30 (s, Me))

Boc-(3-Ph)-Pro-OH was synthesized by a method similar to that of J. Y. L. Chung et al. (J. Y. L. Chung et al. J.Org.Chem. 55 (1990) 270).

Preparation of Boc-1-tetralinylglycine

Boc-1-Tetralinylglycine was prepared starting from 1,2-dihydronaphthalene. 1,2-dihydronaphthalene was initially converted into 1-tetralyl bromide with HBr (similar to J. Med. Chem. 37 (1994) 1586). The bromide was subsequently reacted with diethyl acetamidomalonate and, after hydrolytic cleavage, the resulting α-amino acid was converted into the Boc-protected form under standard conditions. Another possible preparation is described by E. Reimann and D. Voss (E. Reimann, D. Voss, Arch. Pharm. 310 (1977) 102).

Preparation of Boc-1-(D,L)Tic-OH

Boc-1-(D,L)Tic-OH was prepared by a method of R. T. Shuman et al. (R. T. Shuman et al. J. Med. Chem. 36 (1993) 314).

Preparation of Boc-(D,L)Dch-OH

Boc-(D,L)-Dpa-OH (1 mmol) was hydrogenated in 12 ml of MeOH together with catalytic amounts of 5% Rh/$Al_2O_3$ under 5 bar. Filtration and removal of the solvent under reduced pressure resulted in the product in quantitative yield.

Preparation of Cycloheptylglycine, Cyclopentylglycine, 4-Isopropylcyclohexylglycine and 3,3-Dimethylcyclohexylglycine These amino acids were prepared by reacting cycloheptanone, cyclopentanone, 4-isopropylcyclohexanone and 3,3-dimethylcyclohexanone, respectively, with ethyl isonitrileacetate [sic] by a method of H. J. Prätorius (H. J. Prätorius, J. Flossdorf, M. Kula, Chem. Ber. 108 (1985) 3079).

Preparation of H-D,L-Chea-OH 4.0 g of cycloheptylmethyl methanesulfonate (19.39 mmol), prepared from cycloheptylmethanol and methanesulfonyl chloride, were refluxed together with 4.9 g of benzophenone imine glycine ethyl ester [sic] (18.47 mmol), 8.9 g of dry, finely powdered potassium carbonate (64.65 mmol) and 1 g of tetrabutylammonium bromide (3 mmol) in 50 ml of dry acetonitrile under an inert gas atmosphere for 10 h. The potassium carbonate was then filtered off, the filtrate was evaporated to dryness, and the crude product was hydrolyzed directly with 20 ml of 2N hydrochloric acid in 40 ml of ethanol, stirring at RT for 1.5 h. The reaction solution was diluted and then benzophenone was extracted with ethyl acetate in the acidic range, and subsequently H-D,L-Chea-OEt was extracted with DCM in the alkaline range (pH=9), and the solution was dried over magnesium sulfate and concentrated in a rotary evaporator. Yield 3.7 g=95% of theory.

Boc-(D,L)-(3,4,5-(MeO)$_3$)Phe-OH was prepared by alkylation of benzophenone imine glycine ethyl ester [sic] with trimethoxybenzyl chloride, subsequent introduction of the Boc protective group and ester hydrolysis.

D-(1,4-Cyclohexadien-1-yl)ala-OH [sic] was prepared by the method of G. Zivilichovsky, V. Gurvich J. Chem. Soc., Perkin Trans I 19 (1995) 2509–15.

H-(D,L)-ββ-Me$_2$Cha-OH was prepared by the method of U. Schöllkopf, R. Meyer, L. Ann. Chem. (1977) 1174–82.

Said amino acids were converted with di-tert-butyl dicarbonate in water/dioxane by conventional methods into the Boc-protected form in each case and subsequently recrystallized from ethyl acetate/hexane mixtures or purified by column chromatography on silica gel (mobile phases: ethyl acetate/petroleum ether mixtures).

The Boc-protected amino acids were employed as B building blocks as shown in Scheme I.

Said amino acids as B building blocks were also in some cases converted into the corresponding benzyl esters and linked to the appropriately protected A building blocks. In the case of compounds with an N—H functionality which was still free, this was subsequently protected with a Boc group, the benzyl ester group was removed by hydrogenation, and the building block A-B-OH was purified by crystallization, salt precipitation or column chromatography. This route is described by way of example for tBuOOC-CH$_2$-(Boc)(D)Cha-OH below.

Synthesis of D-cyclohexylalanine Benzyl Ester

A suspension of 100 g (481 mmol) of D-cyclohexylalanine hydrochloride, 104 g (962 mmol) of benzyl alcohol and 109.7 g (577 mmol) of p-toluenesulfonic acid monohydrate in 2200 ml of toluene was slowly heated to reflux with a water separator. Evolution of hydrogen chloride and dissolving of the suspension to give a clear solution were observed in the temperature range 80–90° C. When no further water separated out (about 4 h), 500 ml of toluene were distilled out, the reaction mixture was allowed to cool overnight, and the resulting residue was filtered off and washed twice with 1000 ml of hexane each time. The resulting residue (195 g) was then suspended in 2000 ml of dichloromethane and, after addition of 1000 ml of water, adjusted to pH 9–9.5 by gradual addition of 50% strength sodium hydroxide solution while stirring. The organic phase was separated off, washed twice with 500 ml of water each time, dried over sodium sulfate and filtered to remove desiccant, and concentration of the filtrate resulted in 115 g (94%) of the title product as pale oil.

N-(tert-butyloxycarbonylmethylene)-D-cyclohexylalanine [sic] Benzyl Ester 115 g (440 mmol) of D-cyclohexylalanine benzyl ester were dissolved in 2000 ml of acetonitrile and, at room temperature, 607.5 g (4.40 mol) of potassium carbonate and 94.3 g (484 mmol) of tert-butyl bromoacetate were added, and the mixture was stirred at this temperature for 3 days. Carbonate was filtered off, washing with acetonitrile, the mother liquor was concentrated (30° C., 20 mbar), the residue was taken up in 1000 ml of methyl tert-butyl ether, and the organic phase was extracted with 5% strength citric acid and saturated sodium bicarbonate solution. The organic phase was dried over sodium sulfate, filtered to remove desiccant and concentrated, and the resulting oil (168 g) was employed directly in the next reaction.

N-Boc-N-(tert-butyloxycarbonylmethylene)-D-cyclohexylalanine [sic] Benzyl Ester

The oil (168 g, 447 mmol) obtained in the previous synthesis was dissolved in 1400 ml of acetonitrile and, after addition of 618 g (4.47 mmol) of potassium carbonate powder and 107.3 g (492 mmol) of di-tert-butyl dicarbonate, stirred at room temperature for 6 days. The potassium carbonate was filtered off with suction, washing with about 1000 ml of acetonitrile, and the filtrate was concentrated. 230 g of the required product were obtained.

N-Boc-N-(tert-butyloxycarbonylmethylene)-D-cyclohexylalanine [sic] Cyclohexylammonium Salt 115 g of N-Boc-N-(tert-butyloxycarbonylmethylene)-D-cyclohexylalanine [sic] benzyl ester were dissolved in 1000 ml of pure ethanol and hydrogenated in the presence of 9 g of 10% Pd on active carbon with hydrogen under atmospheric pressure at 25–30° C. for 2 h. Filtration and removal of the solvent in a rotary evaporator resulted in 100 g (260 mmol) of a yellow oil which was taken up in 1600 ml of acetone and heated to reflux. The heating bath was removed, and a solution of 27 g (273 mmol) of cyclohexylamine in acetone was quickly added through a dropping funnel.

The required salt crystallized out on cooling the reaction mixture to room temperature. The solid was filtered off, washed with 200 ml of acetone and, for final purification, recrystallized once more from acetone. Drying of the residue in a vacuum oven at about 30° C. resulted in 70.2 g of the required salt as white powder.

N-Boc-N-(tert-butyloxycarbonylmethylene)-D-cyclohexylglycine [sic] cyclohexylammonium salt was prepared in a similar way from cyclohexylglycine as precursor.

N-Boc-N-(tert-butyloxycarbonylethylene)-D-cyclohexylalanine [sic] Cyclohexylammonium Salt a) tert-Butyl 3-bromopropionate 16.64 g (109 mmol) of bromopropionic acid, 150 ml of condensed 2-methylpropene and 2 ml of concentrated sulfuric acid were placed at –30° C. under a countercurrent of nitrogen in a glass vessel suitable for an autoclave, tightly closed and stirred at room temperature for 72 h. For workup, the reaction vessel was again cooled to –30° C., and the solution was cautiously poured into 200 ml of ice-cold saturated sodium bicarbonate solution. Excess 2-methylpropene was allowed to evaporate off with stirring, the residue was extracted three times with 50 ml of dichloromethane each time, the combined organic phases were dried over sodium sulfate, the desiccant was filtered off, and the solution was concentrated under water pump vacuum. The oily residue was purified by column chromatography (mobile phase n-hexane, later n-hexane/diethyl ether 9:1). 18.86 g of the title compound were obtained.

b) N-(tert-Butyloxycarbonylethylene)-D-cyclohexylalanine [sic] benzyl ester 49.4 g (189 mmol) of D-cyclohexylalanine benzyl ester were dissolved in 250 ml of acetonitrile and, after addition of 31.6 g (151 mmol) of tert-butyl bromopropionate at room temperature, refluxed for 5 days. The resulting precipitate was filtered off and washed several times with acetonitrile, the filtrate was concentrated under water pump vacuum, the residue was taken up in 350 ml of dichloromethane, and the organic phase was extracted with 5% strength citric acid and saturated sodium bicarbonate solution. The organic phase was dried over sodium sulfate, filtered to remove desiccant and concentrated. The oily residue was purified by column chromatography (mobile phase dichloromethane, later dichloromethane/methanol 95:5). A slightly impure oil was obtained and was employed directly in the next reaction.

c) N-Boc-N-(tert-Butyloxycarbonylethylene)-D-cyclohexylalanine [sic] benzyl ester The oil obtained in the previous synthesis (30 g, max. 70 mmol) was dissolved in 150 ml acetonitrile and, after addition of 28 ml (160 mmol) of diisopropylethylamine and 19.2 g (88 mmol) of di-tert-butyl dicarbonate, stirred at room temperature for 3 days. The reaction mixture was concentrated in a rotary evaporator under water pump vacuum, the residue was taken up in n-hexane and washed five times with 3 ml of a 5% strength citric acid solution each time, the combined organic phases were dried over sodium sulfate, the desiccant was filtered off, and the residue after concentration was subjected to separation by column chromatography (mobile phase hexane/ethyl acetate 95:5). 32.66 g (64 mmol) of the required product were obtained.

d) N-Boc-N-(tert-Butyloxycarbonylethylene)-D-cyclohexylalanine [sic] cyclohexylammonium salt 32.66 g (64 mmol) of N-Boc-N-(tert-butyloxycarbonylethylene)-D-cyclohexylalanine [sic] benzyl ester were dissolved in 325 ml of pure ethanol and hydrogenated with hydrogen under atmospheric pressure at 25–30° C. in the presence of 3 g of 10% Pd on active carbon for 14 h. Filtration of the solution through Celite®, washing with ethanol and removal of the solvent in a rotary evaporator resulted in 26.7 g of a yellow oil, which was taken up in acetone and heated to reflux. The heating bath was removed, and a solution of 7 g (70 mmol) of cyclohexylamine in acetone was quickly added through a dropping funnel. The required salt crystallized out on cooling the reaction mixture to room temperature. The solid was filtered off, washed with 25 ml of acetone and, for final purification, recrystallized once more from acetone. Drying of the residue in a vacuum oven at 30° C. resulted in 26.6 g (54 mmol) of the required salt as white powder.

N-Boc-N-(tert-Butyloxycarbonylmethylene)-(D)-cyclohexylalanyl-3,4-dehydroproline [sic]

a) N-Boc-Pyr-OH (5 g, 23.45 mmol) was dissolved in MeOH (50 ml), and HCl in dioxane (4N, 30 ml) was added. After refluxing for 12 h, the solvent was removed in a rotary evaporator and H-Pyr-OMe hydrochloride was obtained as product. Yield: 3.84 g (100%).

b) N-(t-BuO$_2$C—CH$_2$)-N-Boc-(D)-Cha-OH (8 g, 20.75 mmol) was dissolved in dichloromethane (75 ml) and, at −10° C., ethyl diisopropylamine (15.5 ml, 89.24 mmol) was added. After stirring at this temperature for 5 min, a solution of H-Pyr-OMe hydrochloride (3.4 g, 20.75 mmol) in dichloromethane (25 ml) was added dropwise. A solution of propanephosphonic anhydride in ethyl acetate (50% strength, 20 ml, 26.96 mmol) was then added dropwise, and the mixture was stirred at −10 to 0° C. for 2 h. The mixture was diluted with dichloromethane and washed with saturated sodium bicarbonate solution (2×80 ml), 5% citric acid solution (2×15 ml) and saturated sodium chloride solution (1×20 ml). The organic phase was dried over sodium sulfate, and the solvent was removed in a rotary evaporator. The crude product was purified by flash chromatography (silica gel, dichloromethane/methanol=95/5). Yield:6.2 g (60%).

c) N-(t-BuO$_2$C—CH$_2$)-N-Boc-(D)-Cha-Pyr-OMe (5.5 g, 11.12 mmol) was dissolved in dioxane (40 ml) and, after addition of sodium hydroxide solution (1N, 22.2 ml, 22.24 mmol), stirred at room temperature for 2 h. The dioxane was removed in a rotary evaporator, and the aqueous phase was washed with ethyl acetate and acidified to pH 1–2 with potassium bisulfate solution (20% strength). The aqueous phase was extracted with dichloromethane, and the combined organic phases were dried over sodium sulfate. Yield: 5 g (94%) of colorless foam. Recrystallization from n-hexane saturated with water afforded colorless crystals (m.p.=158–160° C.).

N-Boc-N-(tert-butyloxycarbonylmethylene)-(D)-cyclohexylglycyl-3,4-dehydroproline [sic]

This compound was prepared in a similar way from N-Boc-N-(tert-butyloxycarbonylmethylene)-(D)-cyclohexylglycine [sic] and 3,4-dehydroproline methyl ester.

(L)3,4-Dehydroproline employed as E building block can be purchased, and (D,L)-4,5-dehydropipecolic acid can be prepared by the method of A. Burgstahler, C. E. Aiman, J. Org. Chem. 25 (1960) 489 or C. Herdeis, W. Engel Arch. Pharm. 326 (1993) 297 and subsequently converted with (Boc)$_2$O into Boc-(D,L)-Dep-OH.

The D building blocks were synthesized as follows:

5-Aminomethyl-2-cyanothiophene

Preparation of this building block was carried out as described in WO 95/23609.

4-Aminomethyl-2-cyanothiophene a) 2-Bromo-4-formylthiophene 36 g (320 mmol) of 3-formylthiophene were dissolved in 600 ml of methylene chloride and cooled to 5° C., 100 g (750 mmol) of aluminum trichloride were added in portions, and the reaction mixture was then refluxed. A solution of 59 g (19 ml, 360 mmol) of bromine in 40 ml of methylene chloride was added dropwise over the course of 45 min, and the reaction was allowed to continue under reflux for 4 h. After cooling, the reaction solution was poured into 600 g of ice-water and extracted with methylene chloride, and the organic phase was washed with saturated sodium bicarbonate solution, dried over magnesium sulfate and concentrated in a rotary evaporator. 64.5 g of crude product were obtained and were purified by column chromatography (silica gel, methylene chloride/petroleum ether) to result in a total of 56.5 g of slightly impure product.

b) 2-Cyano-4-formylthiophene 7.6 g (85 mmol) of copper(I) cyanide were added to a solution of 13.53 g (70.82 mmol) of 2-bromo-4-formylthiophene in 25 ml of DMF, and the reaction mixture was refluxed for 3.5 h, during which the originally pale green suspension changed into a black solution. After addition of water, the reaction mixture was extracted several times with ethyl acetate, and the organic phases were combined, washed with saturated brine, dried over sodium sulfate and concentrated in a rotary evaporator under gentle vacuum. Addition of ether to the residue (7 g) resulted in 1.6 g of pure product. The mother liquor was purified together with the crude products from other batches by chromatography (silica gel, methylene chloride/petroleum ether 1:1). A total of 56.5 g of 2-bromo-4-formylthiophene was reacted to give 12.6 g of pure 2-cyano-4-formylthiophene (31% yield).

c) 2-Cyano-3-hydroxymethylthiophene 3.47 g (91.8 mmol) of sodium borohydride were added in portions to a suspension of 12.6 g (91.8 mmol) of 2-cyano-4-formylthiophene in 200 ml of ethanol, and the reaction mixture was stirred at room temperature for 2 h, during which it slowly formed a clear solution. The residue after concentration under reduced pressure was taken up in ethyl acetate and washed successively with saturated brine, 5% strength citric acid and saturated brine, and the organic phase was dried with sodium sulfate and concentrated under reduced pressure to result in 11.7 g of almost pure product (yield 91.5%).

d) 3-Bromomethyl-2-cyanothiophene 11.7 g (84.07 mmol) of 2-cyano-3-hydroxymethylthiophene were dissolved together with 24.1 g (91.87 mmol) of triphenylphosphine in 100 ml of THF at room temperature and, while cooling (ice bath), 30.47 g (91.87 mmol) of tetrabromomethane were added in portions. Stirring at room temperature for 3 hours was followed by concentration under reduced pressure and purification by chromatography on silica gel (methylene chloride/petroleum ether) to result in 18.8 g of pale yellow crystalline product still containing petroleum ether.

e) 4-N,N-Bis(tert-butoxycarbonyl)aminomethyl-2-cyanothiophene 18.81 g of 3-bromomethyl-2-cyanothiophene (crude product, maximum 84.07 mmol) were dissolved in 160 ml of THF and cooled to 5° C., and 3.07 g (102.4 mmol of 80% sodium hydride suspension were added in portions. Subsequently 22.25 g (102.4 mmol) of di-tert-butyl iminodicarboxylate dissolved in 160 ml of THF were added dropwise at 5° C., and the mixture was then stirred at room temperature overnight. Since conversion was incomplete according to TLC, the mixture was heated at 30–35° C. for 4.5 h. After cooling to 0–5° C., 33 ml of saturated ammonium chloride solution were slowly added dropwise, THF was distilled off under reduced pressure, the residue was extracted several times with ethyl acetate, and the ethyl acetate phases were washed with saturated brine, dried over sodium sulfate and concentrated in a rotary evaporator. The viscous red residue (34.61 g) was employed as crude product in the next reaction.

f) 4-Aminomethyl-2-cyanothiophene hydrochloride 34.61 g of 4-N,N-bis(tert-butoxycarbonyl)aminomethyl-2-cyanothiophene (crude product, maximum 84.07 mmol) were dissolved in 600 ml of ethyl acetate, cooled to 0–5° C., saturated with HCl gas and warmed to room temperature. After 3 h, the resulting suspension was concentrated in a rotary evaporator and codistilled several times with methylene chloride, and the residue was extracted by stirring with ether and dried under reduced pressure. 13.85 g of product were obtained as a pale powder. Yield over two stages 94.3%.

2-Aminomethyl-4-cyanothiophene a) 4-Cyanothiophene-2-carbaldehyde 49.3 g (258.05 mmol) of 4-bromothiophene-2-carbaldehyde and 27.8 g (310.41 mmol) of copper(I) cyanide were suspended in 130 ml of absolute DMF and refluxed for 8 h. The solvent was removed in a rotary evaporator at 40° C., and the residue was suspended in ethyl acetate and transferred into a Soxleth [sic] apparatus. The residue was extracted overnight, the yellow solution was dried over sodium sulfate and concentrated in a rotary evaporator, and the resulting yellow solid was recrystallized from ether to result in 25.3 g of product (80% of theory).

b) 4-Cyanothiophene-2-carbaldehyde oxime 11.6 g (84.6 mmol) of 4-cyanothiophene-2-carbaldehyde were dissolved in 140 ml of methanol, and 12.3 g (116.1 mmol) of sodium carbonate were added. Then 6.5 [lacuna] (93.5 mmol) of hydroxylamine hydrochloride were added in portions while cooling at 15° C., and the mixture was stirred at 10° C. for 2 h. After addition of 80 ml of water, the reaction mixture was extracted five times with 50 ml of diethyl ether each time, the organic phase was dried over sodium sulfate, and the solvent was removed under reduced pressure to result in 12.5 g of the required product as yellow crystalline powder (96% of theory).

c) 2-Aminomethyl-4-cyanothiophene hydrochloride 11.22 g (171.64 mmol) of fine zinc dust were added cautiously in several small portions to a solution of 4.65 g (30.60 mmol) of 4-cyanothiophene-2-carbaldehyde oxime in 50 ml of trifluoroacetic acid cooled to 0–5° C. in such a way that the temperature did not exceed 15° C. After stirring at room temperature for 3 h and decantation from excess zinc, the trifluoroacetic acid was substantially removed under reduced pressure (oil pump), the remaining oil was cooled to 0° C., a mixture of 150 ml of 3N sodium hydroxide solution and 2 l of methylene chloride which had been cooled to 0° C. was added in portions. Insolubles were removed by filtration and then the organic phase was separated off, the aqueous phase was extracted eight times with 20 ml of methylene chloride, the collected organic phases were dried over sodium sulfate and then, while cooling in ice, 20 ml of 6M methanolic hydrochloric acid were added. The product precipitated in the form of the hydrochloride as a white solid, and crystallization was completed by cooling the suspension at 4° C. overnight. 2.2 g of product were obtained as colorless needles (50% of theory).

5-Aminomethyl-3,4-dimethylthiophene-2-carboxamide Hydrochloride 19 g (105.42 mmol) of 5-cyano-3,4-dimethylthiophene-2-carboxamide were suspended in 760 ml of methanol and 110 ml of 2N hydrochloric acid solution and, after addition of 9.5 g of Pd on carbon (10%), hydrogenated at room temperature. After uptake of 4.7 l of hydrogen (4 h), methanol was distilled out under reduced pressure, and the aqueous phase was extracted three times with ethyl acetate and then freeze-dried. 16.3 g of the required product were obtained as a white solid (70.4% of theory).

5-Aminomethylisoxazole-3-carboxamide a) Ethyl 5-chloromethylisoxazole-3-carboxylate 21.2 g (210 mmol) of triethylamine were added dropwise to a stirred mixture of 30 g (198 mmol) of ethyl 2-chloro-2-hydroxyiminoacetate and 150 ml of propargyl chloride cooled to 10–15° C. and, after stirring at room temperature for 1 h, water was added, the mixture was extracted with ether, and the organic phase was dried over magnesium sulfate and concentrated in a rotary evaporator. The residue was distilled under 0.5 torr, the product distilling over at 116–122° C.

b) 5-Chloromethylisoxazole-3-carboxylic acid 47.3 g (250 mmol) of ethyl 5-chloromethylisoxazole-3-carboxylate in 150 ml of ethanol were mixed with 14 g (250 mmol) of potassium hydroxide, and the mixture was stirred at 60–70° C. for 6 h. After cooling and concentration under reduced pressure, the residue was taken up in water and extracted with ether, the aqueous phase was acidified with hydrochloric acid and then extracted several times with ether, and the ether phase was dried over sodium sulfate and concentrated under reduced pressure (oil pump, 50° C.). 31 g of the required product were obtained (77% of theory).

c) 5-Chloromethylisoxazole-3-carbonyl chloride 120 g (743 mmol) of 5-chloromethylisoxazole-3-carboxylic acid were refluxed together with 500 ml of thionyl chloride and 2 drops of pyridine for 10 h, then concentrated under reduced pressure and subsequently distilled under 20 torr. The product distilled at 125–133° C. to result in 78 g (58% of theory).

d) 5-Chloromethylisoxazole-3-carboxamide

Ammonia was passed into a solution of 10 g (55.56 mmol) of 5-chloromethylisoxazole-3-carbonyl chloride in 100 ml of methylene chloride at 10–15° C. for 1 h, and the mixture was then stirred at room temperature for 1 h. After the solution had been cooled to 0° C., the precipitate was filtered off with suction and washed with a little cold methylene chloride, and the residue was extracted by stirring with water twice to remove ammonium salts. Drying under reduced pressure resulted in 6.58 g of pure product as a pale powder (74% of theory).

e) 5-Aminomethylisoxazole-3-carboxamide hydrochloride 2.44 g (15.2 mmol) of 5-chloromethylisoxazole-3-carboxamide were added to a mixture of 100 ml of concentrated ammonia solution and 72 ml of methanol, the solution was warmed to 40° C. and, during this, continuously saturated with ammonia gas. The precursor had reacted after 6 h. The methanol was removed under reduced pressure, the aqueous phase was extracted twice with methylene chloride, and then the aqueous phase was carefully evaporated to dryness under reduced pressure. The white solid residue was employed as crude product in the coupling with Boc-dehydroproline.

2-Aminomethylthiazole-4-thiocarboxamide was prepared as described by G. Videnov, D. Kaier, C. Kempter and G. Jung, Angew. Chemie 108, (1996) 1604, deprotecting the N-Boc-protected compound described therein with ethereal hydrochloric acid in methylene chloride.

4-Aminomethylthiazole-2-thiocarboxamide

The precursor ethyl 4-aminomethylthiazole-2-carboxylate was prepared as described in U.S. Pat. No. 4 826 816. After introduction of the Boc protective group on the amine functionality, the ester group was hydrolyzed, the resulting acid functionality was converted via the mixed anhydride (isobutyl carbonate) into the carboxamide and then with Lawesson's reagent into the thioamide. Elimination of the protective group resulted in the intermediate compound indicated above.

5-Aminomethyl-2-cyanofuran a) 5-Cyanofuran-2-carbaldehyde 165 ml (264 mmol) of a 1.6 molar solution of n-butyllithium in n-hexane were added over the course of 20 min to a solution of 26.7 g (264 mmol) of diisopropylamine in 600 ml of tetrahydrofuran cooled to −78° C. The solution was allowed to reach −20° C., again cooled to −75° C. and, at this temperature, a solution of 22.3 g (240 mmol) of 2-cyanofuran in 100 ml of tetrahydrofuran were slowly added dropwise. After stirring for 30 min, 93 ml of dimethylformamide were slowly added dropwise, and the mixture was stirred for a further 30 min. For workup, a solution of 40 g of citric acid in 200 ml of water was added at −70° C. After concentration in a rotary evaporator, 600 ml of saturated sodium chloride solution were added, and the mixture was extracted three times with 200 ml of diethyl ether each time. The combined organic extracts were dried over magnesium sulfate. The desiccant was filtered off and then the solvent was distilled off under water pump vacuum and the residue was purified by column chromatography (mobile phase dichloromethane). The eluate was concentrated and the residue was subjected to steam distillation (boiling range of the azeotrope with water: 60–65° C. at p=0.1 mm Hg). Extraction of the distillate with diethyl ether, drying of the organic phase and concentration of the solution resulted in 10.6 g (88 mmol, 36%) of the title compound. $^1$H-NMR (270 MHz, $d_6$-DMSO): δ=7.7 (d, 1H), 7.8 (d, 1H), 9.75 (s, 1H).

b) 5-Hydroxymethyl-2-cyanofuran 2.34 g (62 mmol) of sodium borohydride were added in portions to a solution of 30 g (0.25 mol) of 5-cyanofuran-2-carbaldehyde in 500 ml of absolute ethanol at −30° C. The solution was stirred at −30° C. for 2 hours and, while cooling, was adjusted to pH 7 with a 5% strength citric acid solution in water. The reaction mixture was concentrated under water pump vacuum, saturated sodium chloride solution was added to the residue, the mixture was extracted several times with 150 ml of diethyl ether each time, the combined organic phases were dried over magnesium sulfate, the desiccant was filtered off, and the solvent was distilled off under water pump vacuum at room temperature. This resulted in 27 g (22 mol, 88%) of the title compound as a dark red oil, which was employed without further purification in the following reactions. $^1$H-NMR (250 MHz, $d_6$-DMSO): δ=4.4 (m, 2H), 5.6 (bs, 1H), 6.6 (d, 1H), 7.5 (d, 1H).

c) 5-Bromomethyl-2-cyanofuran 38 g (145 mmol) triphenylphosphine were added to a solution of 15 g (121 mol [sic]) of 5-hydroxymethyl-2-cyanofuran in 250 ml of tetrahydrofuran. The mixture was cooled to −10° C., and a solution of 48 g (145 mmol) of tetrabromomethane in 100 ml of tetrahydrofuran was added. The mixture was allowed to warm to room temperature and was stirred at this temperature for 3 hours. The mixture was concentrated in a rotary evaporator under water pump vacuum and the residue was purified by column chromatography (mobile phase petroleum ether:dichloromethane 1:1, $R_f$=0.5). 11.5 g of the title compound were obtained. $^1$H-NMR (250 MHz, $d_6$-DMSO): δ=4.8 (m, 2H), 6.7 (d, 1H), 7.7 (d, 1H).

d) 5-N,N-Bis(tert-butoxycarbonyl)aminomethyl-2-cyanofuran 4.0 g (135 mmol) of sodium hydride (80% suspension in mineral oil) were added in portions to a solution of 22.9 g (123 mmol) of 5-bromomethyl-2-cyanofuran in 400 ml of tetrahydrofuran cooled to 0° C. Then a solution of 29.4 g (135 mmol) of di-tert-butyl iminodicarboxylate in 200 ml of tetrahydrofuran was added dropwise, during which the temperature did not exceed 5° C. The mixture was allowed to warm to room temperature and was stirred overnight. Since conversion was incomplete (TLC check), a total of 1.2 g of sodium hydride was added in three portions over a period of 9 hours. To complete the conversion, the mixture was then heated at 35° C. for three hours and, after allowing to cool to room temperature, 600 ml of a saturated ammonium chloride solution were slowly added. The solvent was distilled off under water pump vacuum, the residue was extracted several times with ethyl acetate, and the combined organic phases were washed with saturated sodium chloride solution, dried over magnesium sulfate and concentrated in a rotary evaporator. 37.3 g of an oily residue which still contained di-tert-butyl iminodicarboxylate were obtained and were employed as crude product in the following reaction. $^1$H-NMR (250 MHz, $d_6$-DMSO): δ=1.40, 1.45 (s, 18H), 4.75 (s, 2H), 6.55 (d, 1H), 7.55 (d, 1H).

e) 5-Aminomethyl-2-cyanofuran hydrochloride 37.3 g of 5-N,N-bis(tert-butoxycarbonyl)aminomethyl-2-cyanofuran (crude product from d), maximum 123 mmol) were dissolved in 600 ml of ethyl acetate and cooled to 0° C. The solution was saturated with hydrogen chloride gas, a white precipitate separating out after 30 min. The mixture was allowed to reach room temperature and was stirred overnight, and then the resulting suspension was concentrated in a rotary evaporator, the residue was extracted by stirring with diethyl ether, the solvent was removed by filtration, and the solid residue was dried at room temperature under reduced pressure. 15.1 g of the title compound (77% yield over two stages) were obtained as a pale ocher powder. $^1$H-NMR (250 MHz, $d_6$-DMSO): δ=4.15 (bs, 2H), 6.85 (d, 1H), 7.65 (d, 1H), 8.8–9.0 (bs, 3H).

5-Aminomethyl-3-cyanofuran a) Ethyl 4-oxopentanoate 100 g (0.86 mol) of 4-oxopentanoic acid, 150 g of ethanol and 1 ml of sulfuric acid in 200 ml of benzene were refluxed until water separation in the Dean-Stark trap ceased. The cooled reaction mixture was washed with water, sodium carbonate solution and again with water and then dried under reflux with the Dean-Stark trap. When removal of the water phase was complete, the solvent was removed by distillation and the residue was distilled under reduced pressure. Boiling point 85–87° C./16 mm Hg, yield 105.5 g (85%).

b) Ethyl 4,4-diethoxypentanoate

A mixture of 171.3 g (1.19 mol) of ethyl 4-oxopentanoate, 207 ml (184.2 g, 1.24 mol) of triethyl orthoformate, 26 ml of absolute ethanol and 1 g of p-toluenesulfonic acid was refluxed for 8 h with vigorous stirring and then distilled under reduced pressure. 187.9 g (72.5%) of ethyl 4,4-diethoxypentanoate were obtained, boiling point 104–106° C./14 mm Hg.

c) Ethyl 2-formyllevulinate

A mixture of 106.3 g (0.489 mol) of ethyl 4,4-diethoxypentanoate and 80 ml (73.6 g, 0.99 mol) of ethyl formate was added dropwise to a vigorously stirred suspension of 12.7 g (0.55 gram atom) of sodium (shavings) in 300 ml of anhydrous benzene at 10–15° C. over 3 h. Stirring was continued for a further 3 h, and the reaction mixture was left to stand overnight. 250 ml of water were added with vigorous stirring, and this was continued for a further 15 min. The water layer was separated off, and the benzene layer was extracted with 70 ml of water. The combined aqueous extracts were acidified to pH 2 and extracted with ethyl acetate (5×50 ml), and the organic extracts were dried over calcium chloride.

The ethyl acetate solution was distilled under reduced pressure, and the fraction boiling at 102–110° C./1 mm Hg was collected. This fraction is a mixture of ethyl 2-formyllevulinate and its diethyl ketal. The ratio in the mixture depends on the intensity of the stirring and the duration of the phase separation on isolation of the formylation products.

The benzene layer was likewise dried over calcium chloride, the solvent was removed, and the residue was distilled under reduced pressure, after which the resulting ethyl levulinate/ketal mixture was treated as described in b) in place of the pure ethyl levulinate. Steps (2) and (3a) were repeated until the required amount of ethyl 2-formyllevulinate was obtained.

d) Ethyl 5-methylfuran-3-carboxylate

The abovementioned mixture of ethyl 2-formyllevulinate and its diethyl ketal was dissolved in benzene, the catalyst was added, and the resulting solution was refluxed with a Dean-Stark trap for 3–3.5 h until the water was completely removed. The reaction mixture was then distilled under reduced pressure, resulting in 15 g (97 mmol) of ethyl 5-methylfuran-3-carboxylate, boiling point 97° C./15 mm Hg.

e) 5-Methylfuran-3-carboxylic acid

A mixture of 31.7 g (206 mmol) of ethyl 5-methylfuran-3-carboxylate, 40 ml of 45% strength potassium hydroxide and 100 ml of water was refluxed for 4 h, then cooled to 10° C. and acidified to pH 1 with 15% strength hydrochloric acid. The resulting mixture was left at this temperature for 2 h, and the precipitate was filtered off and dried to constant weight at 45–50° C., resulting in 23.7 g (188 mmol, 91%) of 5-methylfuran-3-carboxylic acid.

f) 5-Methylfuran-3-carbonyl chloride 39.2 g (188 mmol) of phosphorus(V) chloride were added in small portions to a stirred suspension of 23.7 g (188 mmol) of 5-methylfuran-3-carboxylic acid in 100 ml of benzene. Considerable evolution of heat and of hydrogen chloride was observed. The resulting mixture was refluxed for 4 h and then distilled under reduced pressure to result in 24.7 g (171 mmol, 91%) of acid chloride, boiling point 79° C./12 mm Hg.

g) 5-Methylfuran-3-carboxamide 24.7 g (171 mmol) of 5-methylfuran-3-carbonyl chloride were added dropwise to a stirred mixture of 80 ml of a 25% strength ammonium hydroxide solution and 80 ml of benzene at 25–40° C. The resulting mixture was stirred for 3 h and left to stand overnight. The next day, white crystals of the amide were filtered off, washed with cold water and dried to constant weight at 40–45° C. Yield 19.7 g (158 mmol, 92%), melting point 158° C.

h) 5-Methyl-3-cyanofuran 32.9 g of phosphorus(V) chloride were added in small portions to a suspension of 19.7 g (158 mmol) of 5-methylfuran-3-carboxamide in 100 ml of benzene at 30–40° C. The resulting mixture was refluxed until clear (3.5–4 h) and then distilled under reduced pressure. The fraction boiling at 79–140° C./15 mm Hg, was collected. A second distillation afforded 12.7 g (119 mmol, 75%) of the title compound, boiling point 79–80° C./15 mm Hg.

i) 5-Bromomethyl-3-furancarbonitrile 12.7 g (119 mmol) of 5-methyl-3-cyanofuran were dissolved in 100 ml of tetrachaoromethane, and 22 g (122 mmol) of NBS and 12 g (73 mmol) of AIBN were added. The resulting mixture was heated while stirring vigorously to 70° C., when the exothermic reaction started. After the evolution of heat ceased, the reaction mixture was stirred at 80° C. for 3 h and then cooled to room temperature, and the resulting succinimide was filtered off and washed on the filter with tetrachloromethane (2×15 ml).

The solvent was removed under reduced pressure, and distillation of the residue under reduced pressure resulted in 12.7 g (86 mmol, 57%) of 5-bromomethyl-3-furancarbonitrile, boiling point 105° C./1 mm Hg. The $^1$H-NMR spectrum shows that it contains impurities which produce signals at δ 1.3 and 2.2 ppm. The content of these was satisfactorily lower after a second distillation, but about 15% of the product was lost. 5-Bromomethyl-3-furancarbonitrile is a white crystalline substance, melting point 40–45° C. $^1$H-NMR (CDCl$_3$, ppm): 4.41 (2H, CH$_2$), 6.58 (1H, H4), 7.92 1H, H2); 13C-NMR (CDCl$_3$, ppm): 20.86 (CH$_2$), 99.03 (CN or less likely C3), 109.97 (C4), 112.27 (C3 (or CN)), 149.84 (C2), 152.32 (Cm).

The reaction product is highly irritant and must therefore be handled with extreme care.

5-N,N-Bis(tert-butoxycarbonyl)aminomethyl-3-cyanofuran was synthesized in a similar way to 5-N,N-bis(tert-butoxycarbonyl)aminomethyl-2-cyanofuran. Subsequent elimination of the tert-butoxycarbonyl groups was carried out in a saturated solution of hydrogen chloride in chloroform.

2-Amidino-5-(N-Boc-aminomethyl)-1-methylpyrrole Hydroacetate a) 5-Cyano-1-methylpyrrole-2-carbaldehyde 1-methylpyrrole can be converted into 2-cyano-1-methylpyrrole by reaction with chlorosulfonyl isocyanate and dimethylformamide in acetonitrile (see, for example, C. E. Loader et al. Can. J. Chem. 59, (1981) 2673–6). Diisopropylamine (17.5 ml, 124.38 mmol) was introduced into THF (100 ml) under nitrogen. At −78° C., n-butyllithium solution in hexane (15% strength, 75.9 ml, 124.38 mmol) was added dropwise. The mixture was then stirred at −20° C. for 45 min and subsequently cooled to −78° C. again, at which temperature a solution of N-methylpyrrole-2-carbonitrile (12 g, 113.07 mmol) in THF (50 ml) was added dropwise. After stirring at −78° C. for 45 min, DMF (43.9 ml, 546.46 mmol) was added dropwise and stirring was continued at this temperature for 2 h. Addition of citric acid monohydrate (20.56 g) was followed by warming to room temperature and addition of water (112 ml). The THF was removed in a rotary evaporator, and the aqueous phase was saturated with sodium chloride and extracted with diethyl ether (3×200 ml). The combined organic phases were washed with saturated sodium chloride solution and dried over sodium sulfate. The solvent was removed in a rotary evaporator, and the crude product was purified by flash chromatography (silica gel, dichloromethane). Yield: 8.25 g (54%). $^1$H-NMR (CDCl$_3$) δ=4.1 (s, 3H), 6.8 (d, 1H), 6.9 (d, 1H), 9.7 (s, 1H).

b) 5-Hydroxymethyl-1-methylpyrrole-2-carbonitrile

The product (8.2 g, 61.1 mmol) obtained in a) was dissolved in ethanol (200 ml) and, at −10° C., sodium borohydride (2.31 g, 61.13 mmol) was added. After stirring at 0–5° C. for 1.5 h, the solvent was removed in a rotary evaporator and, ice-water and 20% strength sodium bisulfate solution were added to the residue. The aqueous phase was extracted with ethyl acetate. The combined organic phases were washed with saturated sodium bicarbonate solution and water until neutral and dried over sodium sulfate. The solvent was removed in a rotary evaporator and the crude product was purified by flash chromatography (silica gel, dichloromethane/methanol=97.5/2.5). Yield: 7.6 g (91%).

$^1$H-NMR (CDCl$_3$) δ=1.9 (t, 1H), 3.75 (s, 3H), 4.6 (d, 2H), 6.1 (d, 1H), 6.7 (d, 1H).

c) 5-Azidomethyl-1-methylpyrrole-2-carbonitrile

The product (7.5 g, 55.08 mmol) obtained in b) was dissolved in DMF (220 ml) and, at 0° C., triphenylphosphine (43.34 g, 165.25 mmol) was added. After stirring at this temperature for 5 min, tetrabromomethane (54.8 g, 165.25 mmol) was added. The mixture was then stirred at 0° C. for 30 min and at room temperature for 1.5 h. After cooling to 0° C., sodium azide (4.37 g, 67.21 mmol) was added, and the mixture was stirred at room temperature for 4.5 h. Saturated sodium chloride solution was added dropwise at 0° C., and the mixture was diluted with ethyl acetate. The organic phase was separated off and the aqueous phase was extracted with diethyl ether. The combined organic phases were washed with water and dried over sodium sulfate. The solvent was removed in a rotary evaporator and the crude product was purified by flash chromatography (silica gel, ethyl acetate/hexane=1/20). Yield: 5.6 g (63%).

$^1$H-NMR (CDCl$_3$) δ=3.75 (s, 3H), 4.35 (s, 2H), 6.2 (d, 1H), 6.7 (d, 1H).

d) 5-Aminomethyl-1-methylpyrrole-2-carbonitrile

The product (4.71 g, 29.25 mmol) obtained in c) was dissolved in methanol (100 ml), and palladium on carbon (10%, 1 g) was is added. The mixture was then hydrogenated with hydrogen under 1 atmosphere for 4 h. The catalyst was filtered off through Celite®, and the filtrate was concentrated in a rotary evaporator. The residue was extracted by stirring with dichloromethane/diethyl ether=1/1. The product was filtered off with suction and dried in a vacuum oven at 35° C. Yield: 2.7 g (68%).

$^1$H-NMR (CDCl$_3$) δ=3.75 (s, 3H), 3.85 (s, 2H), 6.05 (d, 1H), 6.7 (d, 1H).

e) 5-(N-Boc-Aminomethyl)-1-methylpyrrole-2-carbonitrile

The product (2.7 g, 19.97 mmol) obtained in d) was dissolved in dichloromethane (50 ml) and triethylamine (2.8 ml, 19.97 mmol) was added. Then a solution of di-tertiary-butyl dicarbonate (4.36 g, 19.97 mmol) in dichloromethane (30 ml) was added dropwise. After stirring at room temperature for 2 h, water was added, and the aqueous phase was extracted with dichloromethane. The combined organic phases were dried over sodium sulfate and concentrated in a rotary evaporator. The crude product was employed without further purification in the next reaction. Yield: 4.4 g (94%).

$^1$H-NMR (CDCl$_3$) δ=1.45 and 1.55 (each s, total 9H), 3.7 (s, 3H), 4.3 (d, 2H), 4.7 (sbr, 1H), 6.05 (d, 1H), 6.7 (d, 1H).

f) 5-(N-Boc-Aminomethyl)-1-methylpyrrole-2-hydroxyamidine [sic]

The product (4.3 g, 18.27 mmol) obtained in e) was dissolved in methanol/dichloromethane (100 ml, 1/1) and hydroxylamine hydrochloride (3.17 g, 45.61 mmol) was added. Then ethyldiisopropylamine (19.1 ml, 109.65 mmol) was added dropwise at room temperature. After stirring at 40° C. for 12 h and removal of the solvent in a rotary evaporator, water was added to the residue, and the mixture was acidified to pH 5 with acetic acid and extracted with dichloromethane and ethyl acetate. The combined organic phases were dried over sodium sulfate and concentrated in a rotary evaporator. The crude product was purified by flash chromatography (silica gel, dichloromethane/methanol=95/5). Yield: 3.4 g (69%).

$^1$H-NMR (CDCl$_3$) δ=1.4 (s, 9H), 3.7 (s, 3H), 4.3 (d, 2H), 4.7–4.9 (m, 3H), 6.05 (d, 1H), 6.3 (d, 1H), 7.3 (sbr, 1H).

g) 2-Amidino-5-(N-Boc-aminomethyl)-1-methylpyrrole hydroacetate

The product (3.4 g, 12.67 mmol) obtained in f) was dissolved in methanol (150 ml), acetic acid (1.45 ml, 25.31 mmol) and Raney nickel (421 mg) were added. It was then hydrogenated under 1 atmosphere of hydrogen at 50° C. for 5 h. After cooling to room temperature, the catalyst was filtered off through Celite®, and the filtrate was concentrated. The resulting product was employed without further purification in the next reaction. Yield: 3.7 g (94%).

FAB-MS (M+H$^+$): 253.

2-Amidino-4-(N-Boc-aminomethyl)-1-methylpyrrole Hydroacetate a) 5-Cyano-1-methylpyrrole-3-carbaldehyde Aluminum trichloride (24.24 g, 180.86 mmol) was dissolved in nitromethane/dichloromethane (1/1, 320 ml) and, after cooling to –20° C., 1-methylpyrrole-2-carbonitrile (8 g, 75.36 mmol) was added. Then α,α-dichlorodimethyl ether (10.4 g, 90.43 mmol) dissolved in dichloromethane (42 ml) was added dropwise. After the mixture had been stirred at 0° C. for 4 h, it was poured onto ice (200 g). The aqueous phase was extracted with diethyl ether. The combined organic phases were washed with saturated sodium bicarbonate solution, water and saturated sodium chloride solution until neutral. After drying over sodium sulfate, the solvent was removed in a rotary evaporator. The crude product was employed without further purification in the following reactions. Yield: 9.2 g (91%).

$^1$H-NMR (CDCl$_3$) δ=3.8 (s,3H); 7.2 (s,1H); 7.4 (s, 1H); 9.85 (s,1H).

b) 4-Aminomethyl-1-methylpyrrole-2-carbonitrile was prepared starting from 5-cyano-1-methylpyrrole-3-carbaldehyde similar to the synthesis of 5-aminomethyl-1-methylpyrrole-2-carbonitrile. However, the 4-azidomethyl-1-methylpyrrole-2-carbonitrile was advantageously reduced by a Staudinger reaction (see, for example, S. Nagarajan et al., J. Org. Chem. 52 (1987) 5044–6).

c) 2-Amidino-4-(N-Boc-aminomethyl)-1-methylpyrrole hydroacetate was prepared starting from 4-aminomethyl-1-methylpyrrole-2-carbonitrile similar to the synthesis of 2-amidino-5-(N-Boc-aminomethyl)-1-methylpyrrole hydroacetate.

FAB-MS (M+H$^+$): 253.

4-Amidino-2-(N-Boc-aminomethyl)-1-methylpyrrole Hydroacetate a) 4-Cyano-1-methylpyrrole-2-carbaldehyde 1-Methylpyrrole-2-carbaldehyde (10 g, 91.6 mmol) was dissolved in acetonitrile (100 ml) and cooled to –45° C. Chlorosulfonyl isocyanate (38.9 g, 274.9 mmol) in acetonitrile (40 ml) was added dropwise over 40 min. The mixture was then stirred at room temperature for 12 h. After dropwise addition of dimethylformamide (35 ml), the mixture was heated at 50° C. for 1 h. After cooling to room temperature, the reaction mixture was added to ice (200 ml) and 2N sodium hydroxide solution (286 ml). The precipitate which formed was filtered off with suction. The filtrate were [sic] extracted with diethyl ether. The combined ether phases were washed with dilute sodium bicarbonate solution and water until neutral and dried over sodium sulfate. The solvent was distilled off under water pump vacuum, and the residue was combined with the previously obtained precipitate. Recrystallization from petroleum ether afforded 4-cyano-1-methylpyrrole-2-carbaldehyde (4.3 g) (see, for example, C. E. Loader et al. Can. J. Chem. 59 (1981) 2673–6).

$^1$H-NMR (CDCl$_3$)δ=4.0 (s,3H); 7.2 (s,1H); 7.3 (s, 1H); 9.6 (s, 1H).

$^{13}$C-NMR (CDCl$_3$) δ=37.4; 94.1; 114.7; 125.8; 132.2; 135.8; 179.7.

b) 5-Aminomethyl-1-methylpyrrole-3-carbonitrile were prepared starting from 4-cyano-1-methylpyrrole-2-carbaldehyde similar to the synthesis of 5-aminomethyl-1-methylpyrrole-2-carbonitrile.

$^1$H-NMR (DMSO-d$_6$) δ=3.6 (s, 3H), 3.8 (s, 2H), 4.2 (sbr, 2H), 6.4 (s, 1H), 7.6 (s, 1H).

c) 3-Amidino-5-(N-Boc-aminomethyl)-1-methylpyrrole hydroacetate was prepared starting from 5 aminomethyl-1-methylpyrrole-3-carbonitrile similar to the synthesis of 2-amidino-5-(N-Boc-aminomethyl)-1-methylpyrrole hydroacetate.

FAB-MS (M+H$^+$): 253.

5-Aminomethyl-3-cyano-1,2,4-oxadiazole Hydrochloride a) N-Boc-5-Aminomethyl-3-cyano-1,2,4-oxadiazole Ethyl N-Boc-5-aminomethyl-1,2,4-oxadiazole-2-carboxylate (S. Borg et al. J. Org. Chem. 60 (1995) 3112–20) was dissolved in methanol (50 ml). Ammonia was passed into this solution at −10° C. to RT until conversion was complete. The solvent was removed in a rotary evaporator. The resulting crude product was dissolved in dichloromethane (70 ml) and, at −5° C., diisopropylethylamine (2.9 ml, 16.55 mmol) was added. Then trifluoroacetic anhydride (1.06 ml, 7.61 mmol) dissolved in dichloromethane (10 ml) was added dropwise. After the mixture had been stirred at 0° C. for 1.5 h it was diluted with dichloromethane, washed 2× with saturated sodium bicarbonate solution, 2× with 5% strength citric acid solution and 1× with saturated sodium chloride solution and then dried over sodium sulfate. The solvent was removed in a rotary evaporator and the crude product was purified by chromatography (silica gel, dichloromethane:methanol=97.5:2.5). Yield: 1.2 g (80%).

b) 5-Aminomethyl-3-cyano-1,2,4-oxadiazole hydrochloride

The product (0.9 g, 4.0 mmol) obtained in a) was dissolved in dichloromethane (45 ml) and, at RT, 4M hydrochloric acid in dioxane (3.9 ml, 15.61 mmol) was added. After stirring at RT for 16 h, the solvent was removed in a rotary evaporator. Yield: 645 mg (100%).

$^1$H-NMR (DMSO-d$_6$) δ=4.6 (s, 2H), 9.2 (s, 3H).

N-Methyl-5-aminomethylpyrazole-3-carboxamide a) Methyl N-methyl-5-amidopyrazole-3-carboxylate [sic]

N-Methyl-3-methoxycarbonylpyrazole-5-carbonyl chloride (prepared from 3.7 g, 20.09 mmol of N-methyl-3-methoxycarbonyl-3-carboxylic [sic] acid, J. Org. Chem. 54 (1989) 428) was dissolved in toluene and cooled to −10° C. Then, at −10° C. to 0° C., ammonia was passed in until conversion was complete. The solvent was removed in a rotary evaporator. The residue was taken up in ethanol and, after stirring for 15 min, the ethanol was removed in a rotary evaporator, and the residue was dissolved in warm water and precipitated by cooling to 0° C. The precipitate was filtered off with suction, washed with acetone and dried at 45° C. under reduced pressure. Yield: 1.5 g (41%).

b) Methyl N-methyl-5-cyanopyrazole-3-carboxylate

The product (1.5 g, 8.19 mmol) obtained in a) were [sic] taken up in dichloromethane (20 ml). At −10° C., diisopropylethylamine (3.85 ml, 22.11 mmol) was added and, at this temperature, a solution of trifluoroacetic anhydride (1.3 ml, 9.44 mmol) in dichloromethane (5 ml) was added dropwise over 45 min. The mixture was then stirred at 0° C. for 1 h and subsequently diluted with dichloromethane and washed 2× with saturated sodium bicarbonate solution, 2× with 5% strength citric acid solution and 1× with saturated sodium chloride solution. After drying over sodium sulfate, the solvent was removed in a rotary evaporator. Yield: 1.35 g (100%).

EI-MS (M+): 165.

c) N-Methyl-5-cyanopyrazole-3-carboxamide

The product (1.35 g, 8.19 mmol) obtained in b) was introduced into methanol (50 ml) and cooled to −10° C. Ammonia was then passed in for 8 h. After stirring at RT for 12 h, the precursor had completely reacted. The precipitate product was filtered off with suction, washed with cold methanol and dried under reduced pressure. Yield: 1.22 g (100%).

$^1$H-NMR (DMSO-d$_6$) δ=4.0 (s, 3H), 7.4 (s, 1H), 7.5 (s, 1H), 7.8 (s, 1H).

d) N-Methyl-5-aminomethylpyrazole-3-carboxamide

The product (0.4 g, 2.66 mmol) obtained in c) was dissolved in acetic acid (30 ml), and 10% palladium on carbon (78 mg) was added. The mixture was then hydrogenated under atmospheric pressure at RT until conversion was complete. The catalyst was filtered off through Celite®, and the solvent was removed in a rotary evaporator. Yield: 0.4 g (100%).

EI-MS (M+): 154.

EXAMPLE 1

N-(Hydroxycarbonylmethylene)-(D)-cyclohexylalanyl-3,4-dehydroprolyl 5-(2-amidino)-thienylmethylamide [sic] Hydroacetate a) 3,4-Dehydroprolyl 5-(2-cyano)-thienylmethylamide [sic]

Boc-3,4-dehydroproline (5 g, 23.4 mmol) and 5-aminomethyl-2-cyanothiophene hydrochloride (4.5 g, 25.8 mmol) were dissolved in dichloromethane (25 ml) and, at 0° C., ethyldiisopropylamine (28 ml, 163.8 mmol) with [sic] a 50% strength solution of propanephosphonic anhydride in ethyl acetate (24.8 ml, 117 mmol) were added. After stirring at 0° C. for 1 h, the mixture was warmed to room temperature and then stirred at room temperature for 12 h. The reaction mixture was diluted with dichloromethane and washed with sodium bisulfate solution (4×), sodium bicarbonate solution (3×) and saturated sodium chloride solution (1×). After drying over sodium sulfate and removal of the desiccant by filtration, the solvent was distilled off under water pump vacuum. To eliminate the Boc group, the residue was mixed [lacuna] in dichloromethane (95 ml), stirred at room temperature, evaporated to dryness, codistilled twice with dichloromethane, again concentrated and purified by column chromatography. 6.6 g of the required product still containing a small amount of solvent were obtained.

b) N-(tert-Butoxycarbonylmethylene)-(N-Boc)-(D)-cyclohexylalanyl-3,4-dehydroprolyl 5-(2-cyano)-thienylmethylamide [sic]

t-BuO$_2$C—CH$_2$-Boc-(D)-Cha-OH (7.3 g, 18.98 mmol) and H-Pyr-NH—CH$_2$-5-(2-CN)-thioph hydrochloride (5.12 g, 18.98 mmol) were dissolved in dichloromethane (100 ml), and ethyldiisopropylamine (12.26 g, 94.9 mmol) was added. The reaction mixture was cooled to 0° C. and a 50% strength solution of propanephosphonic anhydride in ethyl acetate (20 ml) was added dropwise. Stirring at 0–10° C. for 3 h was followed by dilution with dichloromethane (100 ml) and washing with dilute sodium bisulfate solution (3×), saturated sodium bicarbonate solution (2×) and water (1×). After drying over sodium sulfate and removal of the desiccant, the solvent was distilled off under water pump vacuum. 12.47 g of a pale brownish oil were obtained.

c) N-(tert-Butoxycarbonylmethylene)-(N-Boc)-(D)-cyclohexylalanyl-3,4-dehydroprolyl 5-(2-amidothiocarbonyl)-thienylmethylamide [sic]

The product obtained in b) was dissolved in pyridine (70 ml) and triethylamine (12 ml). The reaction mixture was cooled to 0° C. and saturated with hydrogen sulfide (the solution became green). It was then stirred at room temperature for 48 h. The excess hydrogen sulfide was displaced with nitrogen, and the solvent was distilled off under water pump vacuum. The residue was dissolved in diethyl ether (200 ml) and washed with dilute sodium bisulfate solution (2×), saturated sodium bicarbonate solution (2×) and water (1×). After drying over sodium sulfate, the solvent was distilled off under water pump vacuum. The crude product (12.6 g) was purified by flash chromatography (silica gel, gradient from dichloromethane to dichloromethane:methanol=40:1). 12.1 g of the required product which still contained a small amount of solvent were obtained.

d) N-(tert-Butoxycarbonylmethylene)-(N-Boc)-(D)-cyclohexylalanyl-3,4-dehydroprolyl 5-(2-S-methylimidocarbonyl)-thienylmethylamide [sic] hydroiodide The product obtained in c) was dissolved in dichloromethane (120 ml), and methyl iodide (16.24 g, 114.38 mmol) was added. After stirring at room temperature for 12 h, the solvent was distilled off under water pump vacuum. 14.6 g of a yellowish oil were obtained.

e) N-(tert-Butoxycarbonylmethylene)-(N-Boc)-(D)-cyclohexylalanyl-3,4-dehydroprolyl 5-(2-amidino)-thienylmethylamide [sic] hydroacetate The crude product obtained in d) was dissolved in acetonitrile (90 ml), and ammonium acetate (2.94 g, 38.12 mmol) was added. After stirring at room temperature for 2 h and at 40° C. for 1.5 h, 10% strength ammonium acetate solution in methanol (14.65 g, 19.05 mmol) was added. The mixture was then stirred at 50° C. for 4.5 h, and the solvent was distilled off under water pump vacuum. The residue was mixed with dichloromethane, the salts were filtered off with suction, and the filtrate was concentrated. The residue was converted into the acetate salt on an ion exchanger (Fluka, Order No. 00402), resulting in 11.15 g of a yellowish oil.

f) N-(Hydroxycarbonylmethylene)-(D)-cyclohexylalanyl-3,4-dehydroprolyl 5-(2-amidino)-thienylmethylamide [sic] hydroacetate The product obtained in e) was dissolved in dichloromethane (175 ml), and ethereal hydrochloric acid solution (38.3 ml) was added dropwise. After stirring at room temperature for 2 h, the solvent was distilled off under water pump vacuum. The residue was mixed with dichloromethane, and the solvent was distilled off under water pump vacuum (2×). The crude product (9.35 g) was purified on an ion exchanger (Fluka, Order No. 00402) and subsequent flash chromatograpy (silica gel, gradient from dichloromethane:methanol : [sic] 4:1 via dichloromethane:methanol:50% strength acetic acid : [sic] 40:10:2 to dichloromethane:methanol:50% strength acetic acid= 35:15:5). The product obtained in this way was dissolved in water. Insolubles were removed by filtration, and the filtrate was lyophilized to result in 5.55 g as amorphous white solid.

FAB-MS (m+H$^+$) [sic]: 462

The following were prepared as in Example 1:

EXAMPLE 2

N-(Hydroxycarbonylethylene)-(D)-cyclohexylalanyl-3,4-dehydroprolyl 5-(2-amidino)-thienylmethylamide [sic] Hydroacetate

FAB-MS (M+H$^+$): 476

Prepared over several stages as in Example 1 starting from N-(tert-butoxycarbonylethylene)-(N-Boc)-(D)-cyclohexylalanine [sic] and 3,4-dehydroprolyl 5-(2-cyano)-thienylmethylamide [sic].

EXAMPLE 3

N-(Hydroxycarbonylmethylene)-(D)-cyclohexylglycyl-3,4-dehydroprolyl 5-(2-amidino)-thienylmethylamide [sic] Hydroacetate

FAB-MS (M+H$^+$): 448

Prepared over several stages as in Example 1 starting from N-(tert-butoxycarbonylmethylene)-(N-Boc)-(D)-cyclohexylglycine [sic] and 3,4-dehydroprolyl 5-(2-cyano)-thienylmethylamide [sic].

EXAMPLE 4

N-(Hydroxycarbonylmethylene)-(D)-cyclohexylalanyl-3,4-dehydroprolyl 5-(2-amidino-3,4-dimethyl)-thienylmethylamide [sic] Hydroacetate

FAB-MS (M+H$^+$): 490

Prepared starting from 5-aminomethyl-3,4-dimethylthiophene-2-carboxamide by coupling with Boc-3,4-dehydroproline to give Boc-3,4-dehydroprolyl 5-(2-carbamoyl-3,4-dimethyl)-thienylmethylamide [sic] as in Example 1. After elimination of the Boc protective group, this building block was coupled to N-(tert-butoxycarbonylmethylene)-(N-Boc)-(D)-cyclohexylalanine [sic] as in Example 1. Dehydration of the amide to the nitrile functionality was carried out in the following way:

4.8 g (7.42 mmol) of N-(tert-butoxycarbonylmethylene)-(N-Boc)-(D)-cyclohexylalanyl-3,4-dehydroprolyl 5-(2-carbamoyl-3,4-dimethyl)-thienylmethylamide [sic] were dissolved in 60 ml of methylene chloride and, after addition of 3.83 g (29.64 mmol) of diisopropylethylamine, cooled to 0° C. 2.8 g of trifluoroacetic anhydride in 3 ml of methylene chloride were slowly added dropwise, and the mixture was stirred at 0–5° C. for two hours. The mixture was then diluted with 60 ml of methylene chloride and successively washed three times with 20 ml of 20% strength citric acid, twice with 20 ml of saturated sodium bicarbonate solution and twice with saturated brine, and the methylene chloride phase was dried over sodium sulfate and concentrated in a rotary evaporator. 5.35 g of N-(tert-butoxycarbonylmethylene)-(N-Boc)-(D)-cyclohexylalanyl-3,4-dehydroprolyl 5-(2-cyano-3,4-dimethyl)-thienylmethylamide [sic], which still contained solvent, were obtained and were employed directly in the next stage.

Conversion of the nitrile functionality into the amidine group and subsequent elimination of protective groups took place as in Example 1.

EXAMPLE 5

N-(Hydroxycarbonylmethylene)-(D)-cyclohexylalanyl-3,4-dehydroprolyl 5-(3-amidino)-thienylmethylamide [sic] Hydroacetate

FAB-MS (M+H$^+$): 462

Prepared as in Example 1, employing 5-aminomethyl-3-cyanothiophene hydrochloride in place of 5-aminomethyl-2-cyanothiophene hydrochloride.

EXAMPLE 6

N-(Hydroxycarbonylmethylene)-(D)-cyclohexylalanyl-3,4-dehydroprolyl 4-(2-amidino)-thienylmethylamide [sic] Hydroacetate

FAB-MS (M+H$^+$): 462

Prepared as in Example 1 employing 4-aminomethyl-2-cyanothiophene hydrochloride in place of 5-aminomethyl-2-cyanothiophene hydrochloride.

EXAMPLE 7a

N-(Hydroxycarbonylmethylene)-(D)-cyclohexylalanyl-(D)-4,5-dehydropipecolyl 5-(2-amidino)-thienylmethylamide [sic] Hydroacetate

FAB-MS (M+H$^+$): 476

EXAMPLE 7b

N-(Hydroxycarbonylmethylene)-(D)-cyclohexylalanyl-4,5-dehydropipecolyl 5-(2-amidino)-thienylmethylamide [sic] Hydroacetate

FAB-MS (M+H$^+$): 476

Prepared as in Example 1 employing racemic Boc-(D,L)-4,5-dehydropipecolic acid in place of Boc-3,4-dehydroproline. It was possible at the stage of N-(tert-butoxycarbonylmethylene)-(N-Boc)-(D)-cyclohexylalanyl-(D, L)-4,5-dehydropipecolyl 5-(2-cyano)-thienylmethylamide [sic] to separate the two diastereomeric compounds by chromatography (silica gel, cyclohexane/ethyl acetate 7:3). The two diastereomers were subsequently converted into the final products as in Example 1.

EXAMPLE 8

N-(Hydroxycarbonylmethylene)-(D)-cyclohexylglycyl-3,4-dehydroprolyl 5-(3-amidino)-thienylmethylamide [sic] Hydroacetate

FAB-MS (M+H$^+$): 448

Prepared as in Example 1 starting from 5-aminomethyl-3-cyanothiophene and N-(tert-butoxycarbonylmethylene)-N-Boc-(D)-cyclohexylglycyl-3,4-dehydroproline [sic].

EXAMPLE 9

N-(Hydroxycarbonylmethylene)-(D)-cyclohexylglycyl-3,4-dehydroprolyl 4-(2-amidino)-thienylmethylamide [sic] Hydroacetate

FAB-MS (M+H$^+$): 448

Prepared as in Example 1, starting from 4-aminomethyl-2-cyanothiophene and N-(tert-butoxycarbonyl-methylene)-N-Boc-(D)-cyclohexylglycyl-3,4-dehydroproline [sic].

EXAMPLE 10

N-(Hydroxycarbonylmethylene)-(D)-cyclohexylalanyl-3,4-dehydroprolyl 5-(2-amidino)-furanylmethylamide [sic] Hydroacetate

FAB-MS (M+H$^+$): 446

Prepared as in Example 1 employing 5-aminomethyl-2-cyanofuran hydrochloride in place of 5-aminomethyl-2-cyanothiophene hydrochloride.

EXAMPLE 11

N-(Hydroxycarbonylethylene)-(D)-cyclohexylalanyl-3,4-dehydroprolyl 5-(2-amidino)-furanylmethylamide [sic] Hydroacetate

FAB-MS (M+H$^+$): 460

Prepared as in Example 1 employing 5-aminomethyl-2-cyanofuran hydrochloride in place of 5-aminomethyl-2-cyanothiophene hydrochloride.

EXAMPLE 12

N-(Hydroxycarbonylmethylene)-(D)-cyclohexylglycyl-3,4-dehydroprolyl 5-(2-amidino)-furanylmethylamide [sic] Hydroacetate

FAB-MS (M+H$^+$): 432

EXAMPLE 13

N-(Hydroxycarbonylmethylene)-(D)-cyclohexylalanyl-3,4-dehydroprolyl 5-(3-amidino-furanylmethylamide [sic] Hydroacetate

FAB-MS (M+H$^+$): 446

EXAMPLE 14

N-(Hydroxycarbonylmethylene)-(D)-cyclohexylalanyl-3,4-dehydroprolyl 5-(2-amidino-1-methyl)-pyrrolemethylamide [sic] Hydrochloride a) 5-(N-Boc-Aminomethyl)-1-methylpyrrole-2-amidine [sic] hydroacetate (1.5 g, 4.4 mmol) was dissolved in isopropanol (70 ml) and, after addition of isopropanolic hydrochloric acid (5.5 M, 4.5 ml, 24.0 mmol), heated at 50° C. for 2 h. After cooling to room temperature, the solvent was removed in a rotary evaporator, and the residue was added to a solution of t-BuO$_2$C—CH$_2$-(Boc)-(D)-Cha-Pyr-OH in DMF (50 ml). The solution was cooled to 0° C. and N-methylmorpholine (1.92 ml, 17.44 mmol) was added. Subsequently, TOTU (1.18 g, 3.58 mmol) was added in portions. After stirring at 0° C. for 45 min, the solvent was removed in a rotary evaporator and the crude product was purified by MPLC (RP-18, acetonitrile/water). Yield: 980 mg (45%).

FAB-MS (M+H$^+$): 615 b) The product (550 mg, 0.845 mmol) obtained as in a) was dissolved in dichloromethane (50 ml), and the solution was saturated at 0–5° C. with HCl gas. It was subsequently stirred at 0° C. for 1.5 h. The solvent was removed in a rotary evaporator and the crude product was lyophilized. Yield: 450 mg (100%).

FAB-MS (M+H$^+$): 459

EXAMPLE 15

N-(Hydroxycarbonylmethylene)-(D)-cyclohexylalanyl-3,4-dehydroprolyl 2-(4-amidino-1-methyl)-pyrrolemethylamide [sic] hydrochloride was prepared as in Example 14.

FAB-MS (M+H$^+$): 459.

EXAMPLE 16

N-(Hydroxycarbonylmethylene)-(D)-cyclohexylalanyl-3,4-dehydroprolyl 4-(2-amidino-1-methyl) pyrrolemethylamide [sic] hydrochloride was prepared as in Example 14.

FAB-MS (M+H$^+$): 459.

EXAMPLE 17

N-(tert-Butoxycarbonylmethylene)-(N-Boc)-(D)-cyclohexylalanyl-3,4-dehydroprolyl 2-(4-amidothiocarbonyl)oxazolemethylamide [sic] Hydrochloride a) t-BuO$_2$C—CH$_2$-(Boc)-(D)-Cha-Pyr-OH (2.36 g, 4.92 mmol) was dissolved in dichloromethane (60 ml). At −10° C., diisopropylethylamine (4.3 ml, 24.59 mmol) was added dropwise. After stirring at this temperature for 5 min, 2-aminomethyloxazole-4-thiocarbamide [sic] hydrochloride (1 g, 5.16 mmol, G. Videnov et al. Angew. Chem. 108 (1996) 1604–9, the Boc group in the N-Boc-2-aminomethyloxazole-4-thiocarbamide [sic] described in this reference was cleaved with ethereal hydrochloric acid, and the corresponding hydrochloride was obtained by concentration) was added and then a 50% strength solution of propanephosphonic anhydride in ethyl acetate (5.06 ml, 6.39 mmol) diluted with dichloromethane (10 ml) was added dropwise over 20 min. Stirring at 0° C. for 1 h was followed by warming to RT for 3 h. The mixture was diluted with dichloromethane, washed 2× with saturated sodium bicarbonate solution, 2× with 5% strength citric acid solution and 1× with saturated sodium chloride solution and dried over sodium sulfate. The solvent was removed in a rotary evaporator and the crude product was purified by chromatography (silica gel, dichloromethane: methanol=95:5) (Yield: 2.5 g (82%)).

$^1$H-NMR (DMSO-d$_6$) δ=0.5–2.0 (m, 31H), 3.1–5.5 (m, 8H), 5.8–6.2 (m, 2H), 8.5–9.3 (m, 3H), 9.8 (sbr, 1H).

b) N-(tert-Butoxycarbonylmethylene)-(N-Boc)-(D)-cyclohexylalanyl- 3,4-dehydroprolyl 2-(4-amidino)oxazolemethylamide [sic] hydroacetate The product obtained in a) was dissolved in acetone (50 ml) and, after addition of methyl iodide (1.97 ml, 31.29 mmol), refluxed for 2 h. The solvent and the excess methyl iodide were removed in a rotary evaporator. The resulting crude product was dissolved in tetrahydrofuran (50 ml) and, after addition of ammonium acetate (466 mg, 6.05 mmol), heated at 60° C. for 1.5 h. The solvent was removed in a rotary evaporator and the crude product was converted into the acetate using an ion exchanger (acetate on polymeric support, Fluka 00402), followed by purification by chromatography (silica gel, dichloromethane:methanol:acetic acid= 75:20:5). Yield: 2.0 g (75%).

FAB-MS (M+H$^+$): 603.

c) N-(Hydroxycarbonylmethylene)-(D)-cyclohexylalanyl-3,4-dehydroprolyl 2-(4-amidino)oxazolemethylamide [sic] hydrochloride The product (1.95 g, 2.94 mmol) obtained in b) was dissolved in dichloromethane (50 ml) and 4M hydrochloric acid in dioxane (3.7 ml, 14.71 mmol) was added. After stirring at RT for 20 h, the solvent was removed in a rotary evaporator, and the crude product was dissolved in water and lyophilized. Yield: 1.5 g (100%).

13-H-NMR [sic] (DMSO-d$_6$) δ=168.6, 167.8, 166.2, 162.2, 156.4, 144.7, 129.6, 127.7, 125.5, 67.9, 55.0, 53.5, 45.3, 36.4, 35.7, 33.0, 32.5, 32.0, 25.7, 25.4, 25.2.

EXAMPLE 18

N-(Hydroxycarbonylmethylene)-(D)-cyclohexylalanyl-3,4-dehydroprolyl 5-(3-amidino)-1,2,4-oxadiazolemethylamide [sic] Hydrochloride a) N-(tert-Butoxycarbonylmethylene)-(N-Boc)-(D)-cyclohexylalanyl-3,4-dehydroprolyl 5-(3-cyano)-1,2,4-oxadiazolemethylamide [sic]

N-(t-BuO$_2$C—CH$_2$)-N-Boc-(D)-Cha-Pyr-OH (1.93 g, 4.0 mmol) was dissolved in dichloromethane (65 ml) and, at −10° C., diisopropylethylamine (3.1 ml, 17.67 mmol) was added. Then 5-aminomethyl-3-cyano-1,2,4-oxadiazole hydrochloride (645 mg, 4.0 mmol) dissolved in dichloromethane (30 ml) was added. After stirring for 5 min, a 50% strength solution of propanephosphonic anhydride in ethyl acetate (3.9 ml, 4.93 mmol) diluted with dichloromethane (15 ml) was added dropwise over 30 min. After 1 h at 0° C., the mixture was diluted with dichloromethane and washed 2× with saturated sodium bicarbonate solution, 2× with 5% strength citric acid solution and 1× with saturated sodium chloride solution. After drying over sodium sulfate, the solvent was removed in a rotary evaporator and the crude product was purified by chromatography (silica gel, dichloromethane:methanol=95:5). Yield: 1.55 g (71%).

FAB-MS (M+H$^+$): 587.

b) N-(tert-Butoxycarbonylmethylene)-(N-Boc)-(D)-cyclohexylalanyl-3,4-dehydroprolyl 5-(3-amidino)-1,2,4-oxadiazolemethylamide hydroacetate The product (1.5 g, 2.56 mmol) obtained in a) was dissolved in methanol (5 ml), and acetylcystein (450 mg, 2.76 mmol) was added. Then ammonia was passed in at 35° C. until conversion was complete. The solvent was removed in a rotary evaporator and the crude product was converted into the acetate using an ion exchanger (acetate on polymeric support, Fluka 00402). The resulting crude product was purified by chromatography (RP-18, acetonitrile, water). Yield: 300 mg (18%).

FAB-MS (M+H$^+$): 604.

c) N-(Hydroxycarbonylmethylene)-(D)-cyclohexylalanyl-3, 4-dehydroprolyl 5-(3-amidino)-1,2,4-oxadiazolemethylamide [sic] hydrochloride The product (300 mg, 0.45 mmol) obtained in b) was dissolved in dichloromethane (20 ml) and, at room temperature, a 4M solution of hydrochloric acid in dioxane (0.6 ml, 2.48 mmol) was added. After stirring at RT for 20 h, the solvent was removed in a rotary evaporator, and the product was dissolved in water and lyophilized. Yield: 230 mg (98%).

FAB-MS (M+H$^+$): 448.

EXAMPLE 19

N-(Hydroxycarbonylmethylene)-(D)-cyclohexylalanyl-3,4-dehydroprolyl 5-(3-amidino-N-methylpyrazolemethylamide [sic] Hydrochloride a) N-(tert-Butoxycarbonylmethylene)-(N-Boc)-(D)-cyclohexylalanyl-3,4-dehydroprolyl 5-(3-amido-N-methyl)-pyrazolemethylamide [sic]

N-(t-BuO$_2$C—CH$_2$)-N-Boc-(D)-Cha-Pyr-OH (1.25 g, 2.59 mmol) was introduced into dichloromethane (30 ml). At −10° C., diisopropylethylamine (1.95 ml, 11.16 mmol) was added dropwise. Then a solution of N-methyl-5-aminomethylpyrazole-3-carboxamide (0.4 g, 2.59 mmol) in tetrahydrofuran (20 ml) was added. After stirring for 5 min, a 50% strength propanephosphonic anhydride solution in ethyl acetate (2.36 ml, 3.11 mmol) and dichloromethane (5 ml) were added dropwise over the course of 5 min. Stirring at 0° C. for 45 min was followed by warming to RT for 12 h. The solvent was removed in a rotary evaporator, and the residue was taken up in dichloromethane and washed 2× with saturated sodium bicarbonate solution, 2× with 5% strength citric acid solution and 1× with saturated sodium chloride solution. After drying over sodium sulfate, the solvent was removed in a rotary evaporator, the crude product was purified by chromatography (RP-18, acetonitrile, water). Yield: 220 mg (14%). FAB-MS (M+H$^+$): 617.

b) N-(tert-Butoxycarbonylmethylene)-(N-Boc)-(D)-cyclohexylalanyl-3,4-dehydroprolyl 5-(3-cyano-N-methyl)pyrazolemethylamide [sic]

The product (220 mg, 0.36 mmol) obtained in a) was dissolved in dichloromethane (15 ml) and, at −10° C., diisopropylethylamine (0.17 ml, 0.96 mmol) was added. After stirring for 5 min, a solution of trifluoroacetic anhydride (0.057 ml, 0.41 mmol) in dichloromethane (1 ml) was added dropwise. After 1 h at 0° C., the mixture was diluted with dichloromethane and washed 2× with saturated sodium bicarbonate solution, 2× with 5% strength citric acid solution and 1× with saturated sodium chloride solution. After drying over sodium sulfate, the solvent was removed in a rotary evaporator. Yield: 180 mg (84%).

c) N-(tert-Butoxycarbonylmethylene)-(N-Boc)-(D)-cyclohexylalanyl-3,4-dehydroprolyl 5-(3-amidino-N-methyl)pyrazolemethylamide [sic] hydroacetate The product (180 mg, 0.3 mmol) obtained in b) was dissolved in methanol (1 ml), and acetylcystein (52.8 mg, 0.32 mmol) was added. Then, at 35° C., ammonia was passed in until conversion was complete. The solvent was removed in a rotary evaporator and the crude product was converted into the acetate using an ion exchanger (acetate on polymeric support, Fluka 00402). The crude product was purified by chromatography (RP-18, acetonitrile, water). Yield: 50 mg (16%).

FAB-MS (M+H$^+$): 616.

d) N-(Hydroxycarbonylmethylene)-(D)-cyclohexylalanyl-3,4-dehydroprolyl 5-(3-amidino-N-methyl) pyrazolemethylamide [sic] hydrochloride The product (50 mg, 0.081 mmol) obtained in c) was dissolved in dichloromethane (5 ml), and 5M hydrochloric acid in diethyl ether (0.147 ml) was added. After stirring at RT for 12 h, the solvent was removed in a rotary evaporator and the product was taken up in water and lyophilized. Yield: 40 mg (92%).

FAB-MS (M+H$^+$): 460.

EXAMPLE 20

N-(Hydroxycarbonylmethylene)-(D)-cyclohexylalanyl-3,4-dehydroprolyl 5-(3-amidino) isoxazolemethylamide [sic] Hydrochloride Prepared starting from 5-aminomethylisoxazolyl-3-carboxamide and BOC-3,4-dehydroproline. After coupling and elimination of the BOC protective group, the resulting building block was linked to N-(tert-butoxycarbonylmethylene)-(N-Boc)-(D)-cyclohexylalanine [sic] to give N-(tert-butoxycarbonylmethylene)-(N-Boc)-(D)-cyclohexylalanyl-3,4-dehydroprolyl 5-(3-carbamoyl)-isoxazolemethylamide [sic]. After dehydration of the primary amide to the nitrile function-ality as in Example 4, the amidine was formed as described below.

N-(tert-Butoxycarbonylmethylene)-(N-Boc)-(D)-cyclohexylalanyl-3,4-dehydroprolyl 5-(3-amidino) isoxazolemethylamide [sic] Hydroacetate 1.75 g (3.0 mmol) of N-(tert-butoxycarbonylmethylene)-(N-Boc)-(D)-cyclohexylalanyl-3,4-dehydroprolyl 5-(3-cyano)-isoxazolemethylamide [sic] were dissolved in 10 ml of methanol and, after addition of 0.54 g (3.28 mmol) of N-acetylcystein, refluxed while passing in gaseous ammonia for 4 h. Removal of N-acetylcystein, purification of the product and conversion into the acetate took place by MPL chromatography (RP-18, acetonitrile/water/0.1M acetic acid). Freeze-drying resulted in 1.39 g of white powder (70% of theory).

Deprotection of the purified product with ethereal hydrochloric acid in methylene chloride afforded the title compound compound [sic].

FAB-MS (M+H$^+$): 448.

EXAMPLE 21

N-(Hydroxycarbonylmethylene)-(D)-cyclohexylalanyl-3,4-dehydroprolyl 2-(4-amidino) thiazolemethylamide [sic] Hydroacetate

FAB-MS (M+H$^+$): 463.

Prepared as in Example 1 starting from 2-aminomethylthiazole-4-thiocarboxamide and N-Boc-N-(tert-butyloxycarbonylmethylene)-(D)-cyclohexylalanyl-3,4-dehydroproline [sic].

EXAMPLE 22

N-(Hydroxycarbonylmethylene)-(D)-cyclohexylglycyl-3,4-dehydroproline 2-(4-amidino) thiazolemethylamide [sic] Hydrochloride

FAB-MS (M+H$^+$): 449.

EXAMPLE 23

N-(Hydroxycarbonylmethylene)-(D)-cyclohexylalanyl-3,4-dehydroprolyl 4-(2-amidino) thiazolemethylamide [sic] Hydroacetate

FAB-MS (M+H$^+$): 463.

Prepared as in Example 1 starting from 4-aminomethylthiazole-2-thiocarboxamide and N-(tert-butoxycarbonylmethylene)-N-Boc-(D)-cyclohexylalanyl-3,4-dehydroproline [sic].

EXAMPLE 24

N-(Hydroxycarbonylmethylene)-(D)-cyclohexylglycyl-3,4-dehydroprolyl 4-(2-amidino) thiazolemethylamide [sic] Hydroacetate

FAB-MS (M+H$^+$): 449.

Prepared as in Example 1 starting from 4-aminomethylthiazole-2-thiocarboxamide and N-(tert-butoxycarbonylmethylene)-N-Boc-(D)-cyclohexylglycyl-3,4-dehydroproline [sic].

EXAMPLE 25

N-(Hydroxycarbonylmethylene)-(D)-cyclohexylalanyl-3,4-dehydroprolyl 2-(5-amidino) thiazolemethylamide [sic] Hydroacetate

FAB-MS (M+H$^+$): 463.

Prepared as in EXAMPLE 21.

EXAMPLE 26

N-(Hydroxycarbonylmethylene-(D)-cyclohexylglycyl-3,4-dehydroprolyl 2-(5-amidino) thiazolemethylamide [sic] Hydroacetate

FAB-MS (M+H$^+$): 449.

Prepared as in Example 22.

EXAMPLE 27

N-(Hydroxycarbonylmethylene)-(D)-cyclohexylalanyl-3,4-dehydroprolyl 5-(2-amidino) thiazolemethylamide [sic] Hydroacetate

FAB-MS (M+H$^+$): 463.

Prepared as in Example 23.

EXAMPLE 28

N-(Hydroxycarbonylmethylene)-(D)-cyclohexylglycyl-3,4-dehydrorolyl 5-(2-amidino) thiazolemethylamide [sic] Hydroacetate

FAB-MS (M+H$^+$): 449.

Prepared as in Example 24.

We claim:

1. A compound of the formula I

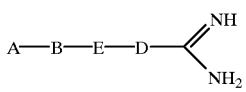

where

A is

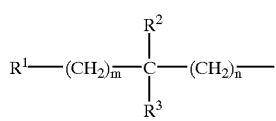

where m is 0, 1 or 2, n is 0, 1 or 2, $R^1$ is HOOC—, $C_{1-6}$-alkyl-OOC—, aryl-$C_1$–$C_4$-alkyl-OOC or —OH, $R^2$ is H, $C_{1-4}$-alkyl or $R^1$-$(CH_2)_m$-, $R^3$ is H or $C_{1-4}$-alkyl, B is

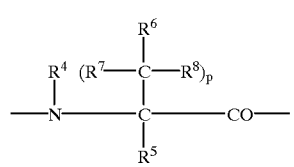

where $R^4$ is H, $C_{1-4}$-alkyl or $R^1$-$(CH_2)_m$- (where $R^1$ and m have the abovementioned meanings), p is 0 or 1, $R^5$ is H or $C_{1-4}$-alkyl, $R^6$ is H, $C_{1-8}$-alkyl, phenyl which may carry up to three identical or different radicals from the group of $C_{1-4}$-alkyl, $CF_3$, $C_{1-4}$-alkoxy, F or Cl, or $C_{3-8}$-cycloalkyl which may carry up to four identical or different $C_{1-4}$-alkyl radicals, or where one or two C—C single bonds in the ring can be replaced by a C=C double bond, or a phenyl ring can be fused on, $C_7$–$C_{12}$-bicycloalkyl or $C_{10}$-tricycloalkyl or $R^4$ and $R^6$ together are an ethylene or propylene group, $R^7$ is H, $C_{1-8}$-alkyl, phenyl which may carry up to three identical or different radicals from the group of $C_{1-4}$-alkyl, $CF_3$, $C_{1-4}$-alkoxy, F or Cl, or $C_{3-8}$-cycloalkyl which may carry up to four identical or different $C_{1-4}$-alkyl radicals, $R^8$ is H or $C_{1-4}$-alkyl, E is

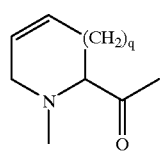

q is 0 or 1

D is

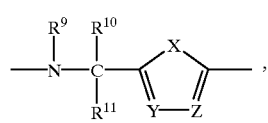

-continued

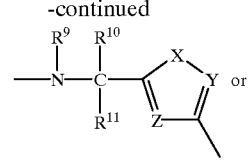

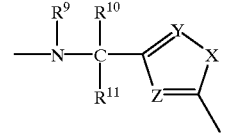

where $R^9$ is H or $C_{1-3}$-alkyl, $R^{10}$ is H or $C_{1-4}$-alkyl, $R^{11}$ is H or $C_{1-4}$-alkyl, X is O, S, —$NR^{12}$ ($R^{12}$=H, $C_{1-6}$-alkyl), Y is —N= or —$CR^{13}$= ($R^{13}$=H, $C_{1-4}$-alkyl), Cl, $CF_3$, Z is —N= or —$CR^{13}$=, and the salts thereof with physiologically tolerated acids.

2. A structural fragment of formula I according to claim 1

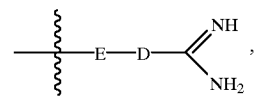

where,

E is

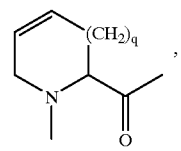

where q is 0 or 1; and

D is

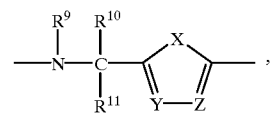

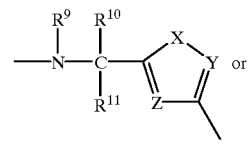

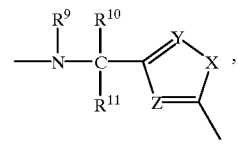

where $R^9$ is H or $C_{1-3}$-alkyl;

$R^{10}$ is H or $C_{1-4}$-alkyl;

$R^{11}$ is H or $C_{1-4}$-alkyl;

X is O, S, —NR$^{12}$ (R$^{12}$=H, C$_{1-6}$-alkyl);

Y is —N= or —CR$^{13}$=(R$^{13}$=H, C$_{1-4}$-alkyl), Cl, CF$^3$; and

Z is —N= or —CR$^{13}$=.

3. A compound of formula IIa or IIb

A—B—E—D—CN                    IIa,

A—B—E—D—CSNH$_2$              IIb where,

A is

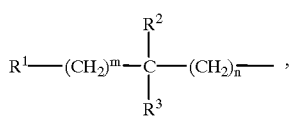

where, m is 0, 1 or 2;

n is 0, 1 or 2;

R$^1$ is HOOC—, C$_{1-8}$-alkyl-OOC—, aryl-C$_1$-C$_4$-alkyl-OOC or —OH;

R$^2$ is H, C$_{1-4}$-alkyl or R$^1$-(CH$_2$)$_m$-;

R$^3$ is H or C$_{1-4}$-alkyl;

B is

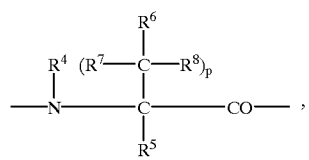

where,

R$^4$ is H, C$_{1-4}$-alkyl or R$^1$-(CH$_2$)$_m$-, where R$^1$ and m have the abovementioned meanings;

p is 0 or 1;

R$^5$ is H or C$_{1-4}$-alkyl;

R$^6$ is H, C$_{1-8}$-alkyl, phenyl which may carry up to three identical or different radicals from the group of C$_{1-4}$-alkyl, CF$_3$, C$_{1-4}$-alkoxy, F or Cl, or C$_{3-8}$-cycloalkyl which may carry up to four identical or different C$_{1-4}$-alkyl radicals, or where one or two C—C single bonds in the ring can be replaced by a C=C double bond, or a phenyl ring can be fused on, C$_7$–C$_{12}$-bicycloalkyl or C$_{10}$-tricycloalkyl; or R$^4$ and R$^6$ together form an ethylene or propylene group;

R$^7$ is H, C$_{1-8}$-alkyl, phenyl which may carry up to three identical or different radicals from the group of C$_{1-4}$-alkyl, CF$_3$, C$_{1-4}$-alkoxy, F or Cl, or C$_{3-8}$-cycloalkyl which may carry up to four identical or different C$_{1-4}$-alkyl radicals;

R$^8$ is H or C$_{1-4}$-alkyl;

E is

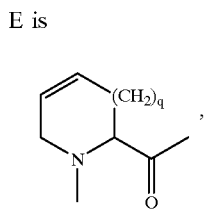

where q is 0 or 1;

D is

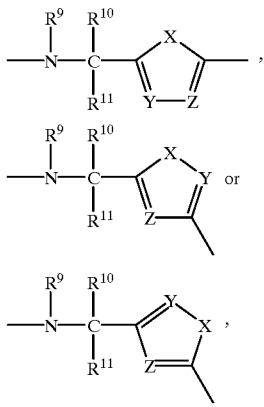

where,

R$^9$ is H or C$_{1-3}$-alkyl;

R$^{10}$ is H or C$_{1-4}$-alkyl;

R$^{11}$ is H or C$_{1-4}$-alkyl;

X is O, S, —NR$^{12}$ (R$^{12}$=H, C$_{1-6}$-alkyl);

Y is —N= or —CR$^{13}$= (R$^{13}$=H, C$_{1-4}$-alkyl), Cl, CF$^3$;

Z is —N= or —CR$^{13}$=;

and the salts thereof with physiologically tolerated acids.

4. The compound of claim 3 which is A—B—E—D—CN.

5. The compound of claim 3 which is A—B—E—D—CSNH$_2$.

6. The compound of formula 1, as defined in claim 1, wherein

A is

HOOC—(CH$_2$)$_t$-(t=1, 2 or 3), (HOOC—CH$_2$)$_2$—CH—, (HO—CH$_2$)$_2$CH—, HOOC—CH$_2$—CH(COOH)—, HOOC—CH(CH$_2$—CH$_2$—OH)—, HOOC—CH(C$_{1-4}$-alkyl)-, HOOC—C(C$_{1-4}$-alkyl)$_2$-, C$_{1-4}$-alkyl-OOC-(CH$_2$), B is

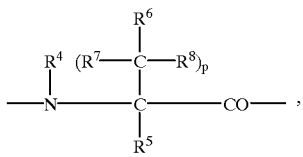

where, p is 0, 1,

R$^4$ is H, C$_{1-4}$-alkyl or HOOC-(CH$_2$)$_m$-(m=1, 2 or 3),

R$^5$ is H, methyl

R$^6$ is H; C$_{1-8}$-alkyl; phenyl which may carry up to three identical or different radicals selected from the group consisting of CH₃, CF₃, CH₃O, F and Cl; C₃₋₈-cycloalkyl which may carry up to four methyl radicals; 1,4-cyclohexadienyl; bicyclo(2.2.2)octyl; bicyclo(2.2.1)heptyl; norbornyl; adamantyl; indanyl; and decalinyl;

R⁷ is H; C₁₋₈-alkyl; phenyl which may carry up to three identical or different radicals selected from the group consisting of CH₃, CF₃, CH₃O, F and Cl; or C₃₋₈-cycloalkyl which may carry up to four methyl radicals;

R⁸ is H, C₁₋₄-alkyl, and

E is

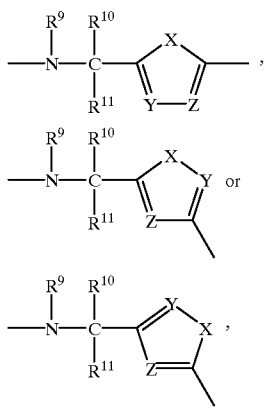

q is 0, 1 and

D is

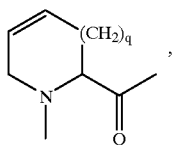,

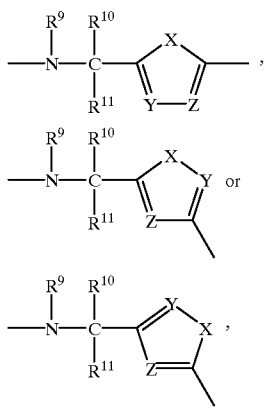 or (second and third D structures shown)

with

X=S, O, NH, NCH₃, NC₂H₅,
Y=CH, C—CH₃, C—Cl, C—CF₃ and
Z=CH, C—CH₃, C—Cl, C—CF₃
or X=S, O, NH, N—CH₃, Y=N, Z=CH, C—CH₃, C—CF₃,
or X=S, O, NH, N—CH₃, Y=CH, C—CH₃, C—CF₃, Z=N,
or X=S, O, NH, N—CH₃, Y=N, Z=N,

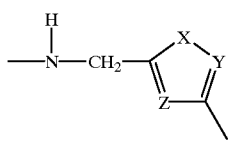

with

X=S, O, NH, NCH₃, NC₂H₅,
Y=CH, C—CH₃, C—CF₃ and
Z=CH, C—CH₃, C—CF₃, C—Cl
or X=O, NH, NCH₃, Y=N, Z=CH, C—CH₃, C=CF₃,
or X=O, NH, NCH₃, Y=CH, C—CH₃, C—CF₃, Z=N,
or X=O, S, NH, NCH₃, Y=Z=N,

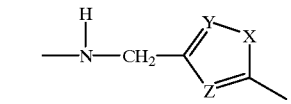

with

X=S, O, NH, NCH₃, NC₂H₅,
Y=CH, C—CH₃, C—CF₃ and
Z=CH, C—CH₃, C—CF₃, C—Cl
or X=O, NH, NCH₃, Y=N, Z=CH, C—CH₃, C—CF₃, C—Cl
or X=O, S, NH, NCH₃, Y=CH, C—CH₃, C—CF₃, Z=N
or X=O, NH, NCH₃, Y=Z=N.

7. The compound of formula 1, as defined in claim 1, wherein

A is HOOC—CH₂, HOOC—CH₂—CH₂, HOOC—CH(CH₃), HOOC—CH(C₂H₅)

B is

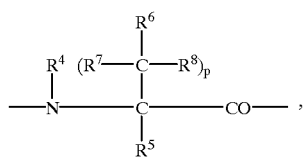

where, p is 0, 1,
R⁴ is H, CH₃,
R⁵ is H, CH₃,
R⁶ is C₁₋₈-alkyl, C₅₋₈-cycloalkyl which may carry up to four methyl radicals, bicyclo(2.2.2)octyl, bicyclo(2.2.1)heptyl, norbornyl, adamantyl, indanyl, decalinyl,
R⁷ is H, CH₃,
R⁸ is H, CH₃, E is

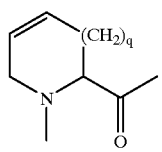

q is 0, 1

D is

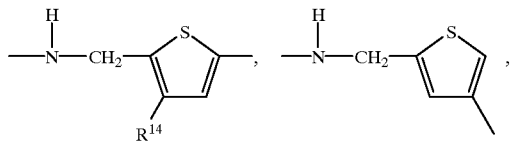

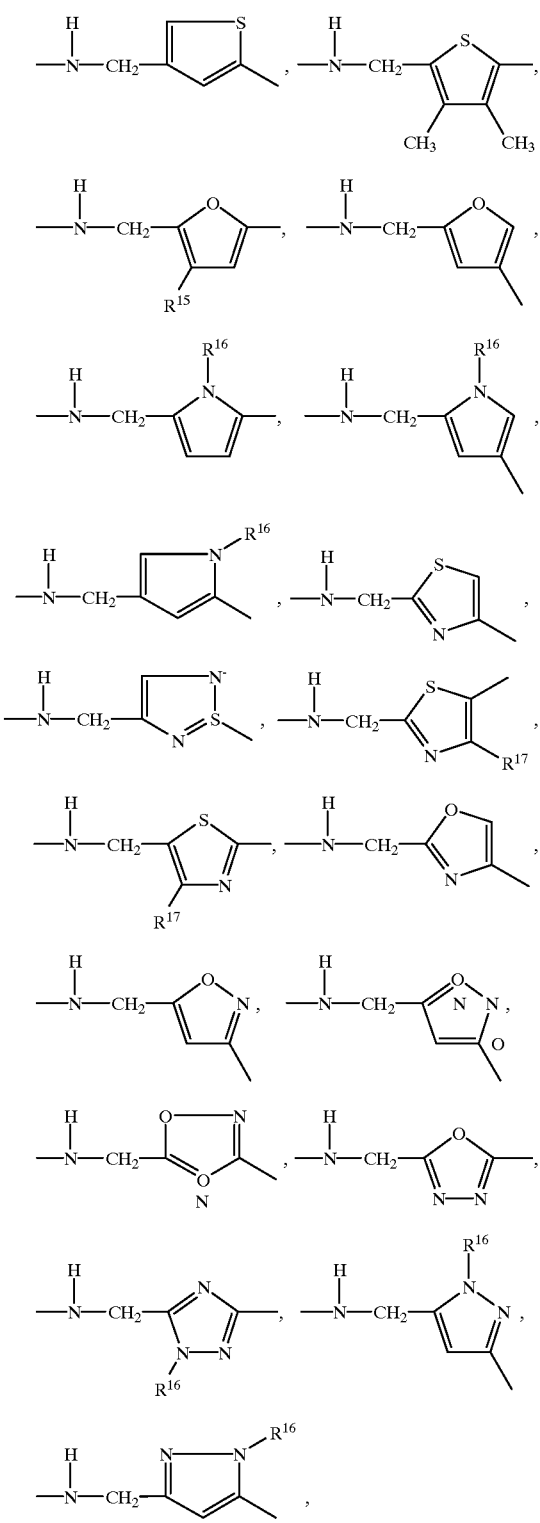

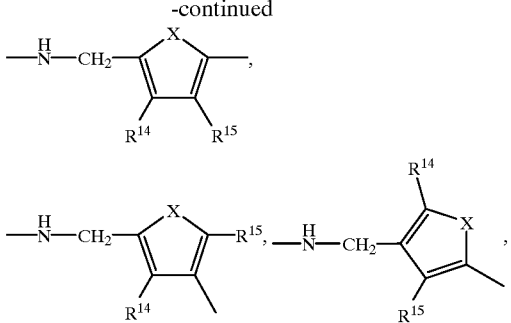

and $R^{14}$ is H, $CH_3$, Cl, $CF_3$, $R^{15}$ is H, Cl, $CF_3$, $R^{16}$ is H, $CH_3$, $C_2H_5$, and $R^{17}$ is H, $CH_3$, $CF_3$.

8. A method of treating the following diseases or conditions: whose pathogenetic mechanism derives directly or indirectly from the proteolytic effect of thrombin; diseases whose pathogenetic mechanism derives from thrombin-dependent activation of receptors and signal transductions; diseases associated with stimulation or inhibition of the expression of genes in body cells; diseases deriving from the mitogenic effect of thrombin; diseases deriving from a thrombin-dependent change in the contractility and permeability of epithelial cells; thrombin-dependent thromboembolic events; disseminated intravascular coagulation; reocclusion and increased reperfusion time on comedication with thrombolytics; the occurrence of early reocclusion and late restenosis after PTCA; the thrombin-dependent proliferation of smooth muscle cells; the accumulation of active thrombin in the CNS; tumor growth and adhesion and metastasis of tumor cells; diseases whose pathogenetic mechanism derives directly or indirectly from the proteolytic effect of a kininogenase inflammatory diseases and other internal diseases in which kallikrein is involved; which method comprises the step of administering to a patient an effective amount of the compound of formula I, as defined in claim 1.

9. The compound of claim 7, wherein $R^6$ is selected from the group consisting of cyclopentyl, cyclohexyl and cycloheptyl.

10. The compound of claim 7 wherein $R^{14}$ is H.

11. The compound of claim 7 wherein $R^{15}$ is H.

12. The compound of claim 7 wherein $R^{16}$ is $CH_3$.

13. The compound of claim 7 wherein $R^{17}$ is H.

14. The compound of claim 7 wherein $R^{17}$ is $CH_3$.

15. The method of claim 8 wherein the kininogenase is kallikrein.

16. The method of claim 8 wherein the inflammatory disease is selected from the group consisting of asthma, pancreatis, rhinitis and urticaria.

* * * * *

UNITED STATES PATENT AND TRADEMARK OFFICE
CERTIFICATE OF CORRECTION

PATENT NO. : 6,114,358
DATED : September 5, 2000
INVENTOR(S) : Baucke et al.

It is certified that error appears in the above-identified patent and that said Letters Patent is hereby corrected as shown below:

Column 41, claim 3,
Line 29, "$C_{1-8}$-alkyl-OOC-" should be --$C_{1-6}$-alkyl-OOC- --.

Column 42, claim 6,
Line 51, "$(CH_2)$" should be --$(CH_2)_t$,--.

Signed and Sealed this

Thirty-first Day of July, 2001

Attest:

NICHOLAS P. GODICI
Attesting Officer     Acting Director of the United States Patent and Trademark Office